US 10,413,445 B2

(12) United States Patent
Scheller et al.

(10) Patent No.: US 10,413,445 B2
(45) Date of Patent: Sep. 17, 2019

(54) ATRAUMATIC MICROSURGICAL FORCEPS

(71) Applicant: Katalyst Surgical, LLC, Chesterfield, MO (US)

(72) Inventors: Gregg D Scheller, Wildwood, MO (US); Carl C Awh, Nashville, TN (US)

( * ) Notice: Subject to any disclaimer, the term of this patent is extended or adjusted under 35 U.S.C. 154(b) by 182 days.

(21) Appl. No.: 15/704,208

(22) Filed: Sep. 14, 2017

(65) Prior Publication Data

US 2018/0000643 A1 Jan. 4, 2018

Related U.S. Application Data

(63) Continuation of application No. 14/953,307, filed on Nov. 28, 2015, now Pat. No. 9,795,506.

(51) Int. Cl.
*A61F 9/007* (2006.01)
*A61B 17/29* (2006.01)
*A61B 17/30* (2006.01)

(52) U.S. Cl.
CPC ...... *A61F 9/00736* (2013.01); *A61B 17/2909* (2013.01); *A61B 2017/2918* (2013.01); *A61B 2017/2926* (2013.01); *A61B 2017/2933* (2013.01); *A61B 2017/2937* (2013.01); *A61B 2017/305* (2013.01)

(58) Field of Classification Search
CPC . A61B 17/00; A61B 2017/2918; A61B 17/29; A61B 17/30; A61B 2017/305; A61F 9/00
USPC ................................. 606/205, 207
See application file for complete search history.

(56) References Cited

U.S. PATENT DOCUMENTS

| | | |
|---|---|---|
| 1,736,731 A | 11/1929 | Breeding |
| 2,549,731 A | 4/1951 | Wattley |
| 3,659,607 A | 5/1972 | Banko |
| 4,135,868 A | 1/1979 | Schainholz |
| 4,504,264 A | 3/1985 | Kelman |
| 4,541,992 A | 9/1985 | Jerge et al. |

(Continued)

FOREIGN PATENT DOCUMENTS

| | | |
|---|---|---|
| WO | WO1997015234 A1 | 5/1997 |
| WO | WO1998037819 A1 | 9/1998 |

(Continued)

OTHER PUBLICATIONS

Steve Charles, Techniques and tools for dissection of epiretinal membranes, Graefe' Arch Clin Exp Ophthalmol, 241:347-352, 2003.

(Continued)

*Primary Examiner* — George J Ulsh

(57) ABSTRACT

An atraumatic microsurgical forceps may include an actuation structure, an actuation sleeve having an actuation sleeve distal end and an actuation sleeve proximal end, a surgical blank, and atraumatic forceps jaws of the surgical blank having atraumatic forceps jaws distal ends and atraumatic forceps jaws proximal ends. The surgical blank may be disposed within the actuation sleeve wherein at least a portion of the atraumatic forceps jaws extends from the actuation sleeve distal end. A compression of the actuation structure may be configured to gradually extend the actuation sleeve over the atraumatic forceps jaws proximal ends. An extension of the actuation sleeve over the atraumatic forceps jaws proximal ends may be configured to gradually close the atraumatic forceps jaws wherein the atraumatic forceps jaws initially contact at the atraumatic forceps jaws distal ends.

20 Claims, 32 Drawing Sheets

(56) References Cited

U.S. PATENT DOCUMENTS

| | | |
|---|---|---|
| 4,553,957 A | 11/1985 | Williams et al. |
| 4,610,252 A | 9/1986 | Catalano |
| 4,706,666 A | 11/1987 | Sheets |
| 4,739,761 A | 4/1988 | Grandon |
| 4,798,292 A | 1/1989 | Hauze |
| 4,959,199 A | 9/1990 | Brewer |
| 5,190,050 A | 3/1993 | Nitzsche |
| 5,215,726 A | 6/1993 | Kudla et al. |
| 5,222,973 A | 6/1993 | Sharpe et al. |
| 5,227,313 A | 7/1993 | Gluck et al. |
| 5,286,255 A | 2/1994 | Webber |
| 5,318,589 A | 6/1994 | Lichtman |
| 5,346,677 A | 9/1994 | Risk |
| 5,355,871 A | 10/1994 | Hurley et al. |
| 5,370,658 A | 12/1994 | Scheller et al. |
| 5,384,103 A | 1/1995 | Miller |
| 5,415,645 A | 5/1995 | Friend et al. |
| 5,425,730 A | 6/1995 | Luloh |
| 5,433,929 A | 7/1995 | Riihimaki et al. |
| 5,451,230 A | 9/1995 | Steinert |
| 5,527,313 A | 6/1996 | Scott et al. |
| 5,601,581 A | 2/1997 | Fogarty et al. |
| 5,636,639 A | 6/1997 | Turturro et al. |
| 5,695,514 A | 12/1997 | Chin |
| D393,067 S | 3/1998 | Geary et al. |
| D393,715 S | 4/1998 | Strickland |
| 5,759,502 A | 6/1998 | Spencer et al. |
| 5,792,165 A | 8/1998 | Klieman et al. |
| 5,810,811 A | 9/1998 | Yates et al. |
| 5,843,387 A | 12/1998 | Dane et al. |
| 5,851,197 A | 12/1998 | Marano et al. |
| 5,893,873 A | 4/1999 | Rader et al. |
| 5,893,877 A | 4/1999 | Gampp, Jr. et al. |
| 5,913,422 A | 6/1999 | Cote et al. |
| 5,916,159 A | 6/1999 | Ryan, Jr. |
| 5,921,998 A | 7/1999 | Tano et al. |
| 6,099,550 A | 8/2000 | Yoon |
| 6,159,162 A | 12/2000 | Kostylev et al. |
| 6,183,467 B1 | 2/2001 | Shapeton et al. |
| 6,277,100 B1 | 8/2001 | Raulerson et al. |
| D453,222 S | 1/2002 | Garito et al. |
| 6,419,675 B1 | 7/2002 | Gallo, Sr. |
| D463,555 S | 9/2002 | Etter et al. |
| 6,488,695 B1 | 12/2002 | Hickingbotham |
| 6,551,129 B2 | 4/2003 | Kato |
| 6,572,565 B2 | 6/2003 | Daley et al. |
| 6,575,989 B1 | 6/2003 | Scheller et al. |
| 6,616,683 B1 | 9/2003 | Toth et al. |
| 6,730,076 B2 | 5/2004 | Hickingbotham |
| 6,749,601 B2 | 6/2004 | Chin |
| 6,800,076 B2 | 10/2004 | Humayun |
| 6,863,668 B2 | 3/2005 | Gillespie et al. |
| 6,908,476 B2 | 6/2005 | Jud et al. |
| 6,926,728 B2 | 8/2005 | Zucherman et al. |
| 6,945,984 B2 | 9/2005 | Arumi et al. |
| 7,338,494 B2 | 3/2008 | Ryan |
| D565,733 S | 4/2008 | Andre |
| 7,438,717 B2 | 10/2008 | Tylke |
| 7,632,242 B2 | 12/2009 | Griffin et al. |
| 7,731,728 B2 | 6/2010 | Glaser |
| 7,783,346 B2 | 8/2010 | Smith et al. |
| D625,412 S | 10/2010 | Garito et al. |
| 7,766,904 B2 | 10/2010 | Mc Gowan, Sr. et al. |
| 7,935,080 B2 | 5/2011 | Howell et al. |
| 8,038,692 B2 | 10/2011 | Valencia et al. |
| 8,197,468 B2 | 6/2012 | Scheller et al. |
| 8,202,288 B2 | 6/2012 | Ryan |
| 8,821,444 B2 | 9/2014 | Scheller et al. |
| 9,138,346 B2 | 9/2015 | Scheller et al. |
| 9,149,389 B2 | 10/2015 | Scheller et al. |
| 9,204,995 B2 | 12/2015 | Scheller et al. |
| 9,226,762 B2 | 1/2016 | Scheller et al. |
| 9,427,251 B2 | 8/2016 | Rethy et al. |
| 2001/0056286 A1 | 12/2001 | Etter et al. |
| 2002/0115902 A1 | 8/2002 | Dejuan, Jr. et al. |
| 2003/0171762 A1 | 9/2003 | Forchette et al. |
| 2003/0229976 A1 | 12/2003 | Scheller et al. |
| 2005/0154403 A1 | 7/2005 | Sauer et al. |
| 2005/0245950 A1 | 11/2005 | Kozlowski |
| 2006/0036270 A1 | 2/2006 | Terao |
| 2006/0235382 A1 | 10/2006 | Cohen et al. |
| 2007/0104609 A1 | 5/2007 | Powell |
| 2007/0106246 A1 | 5/2007 | Modesitt |
| 2007/0185514 A1 | 8/2007 | Kirchhevel |
| 2007/0282348 A1 | 12/2007 | Lumpkin |
| 2008/0183199 A1 | 7/2008 | Attinger |
| 2008/0195135 A1 | 8/2008 | Attinger |
| 2008/0255526 A1 | 10/2008 | Bosse et al. |
| 2009/0030427 A1 | 1/2009 | Razvi et al. |
| 2009/0112258 A1 | 4/2009 | Kreidler |
| 2009/0131870 A1 | 5/2009 | Fiser |
| 2009/0228066 A1 | 10/2009 | Hirata et al. |
| 2009/0318856 A1 | 12/2009 | Glaser |
| 2010/0023050 A1 | 1/2010 | Reinauer et al. |
| 2010/0063359 A1 | 3/2010 | Okoniewski |
| 2010/0145381 A1 | 6/2010 | Moon |
| 2010/0228226 A1 | 9/2010 | Nielsen |
| 2011/0015669 A1 | 1/2011 | Corcosteugi |
| 2012/0116361 A1 | 5/2012 | Hanlon et al. |
| 2012/0150216 A1 | 6/2012 | Hickingbotham et al. |
| 2012/0179172 A1 | 7/2012 | Paul, Jr. et al. |
| 2012/0191120 A1 | 7/2012 | Linsi |
| 2013/0071507 A1 | 3/2013 | Scheller et al. |
| 2013/0085326 A1 | 4/2013 | Scheller et al. |
| 2013/0197488 A1 | 8/2013 | Scheller et al. |
| 2014/0012314 A1 | 1/2014 | Dai et al. |
| 2014/0066977 A1 | 3/2014 | Scheller et al. |
| 2014/0121697 A1 | 5/2014 | Scheller et al. |
| 2014/0128909 A1 | 5/2014 | Scheller et al. |
| 2014/0135820 A1 | 5/2014 | Schaller et al. |
| 2014/0142603 A1 | 5/2014 | Scheller et al. |
| 2014/0163363 A1 | 6/2014 | Scheller et al. |
| 2014/0172010 A1 | 6/2014 | Vezzu |
| 2014/0277110 A1 | 9/2014 | Scheller et al. |
| 2015/0088193 A1 | 3/2015 | Scheller et al. |
| 2015/0173944 A1 | 6/2015 | Linsi et al. |

FOREIGN PATENT DOCUMENTS

| | | |
|---|---|---|
| WO | WO2002041796 A2 | 5/2002 |
| WO | WO2017066026 A1 | 4/2017 |

OTHER PUBLICATIONS http://www.bpf.co.uk/plastipedia/polymers/polyamides.aspx [Mar. 20, 2017 4:57:01 PM].

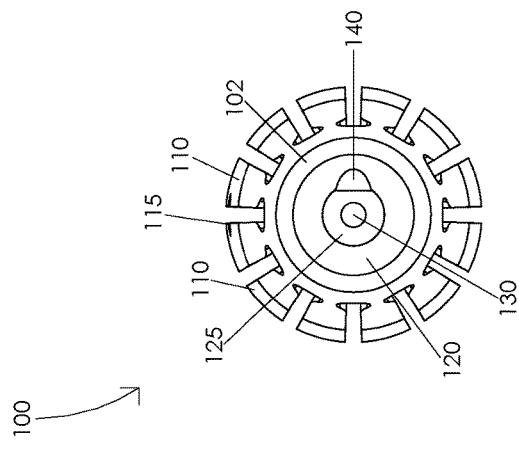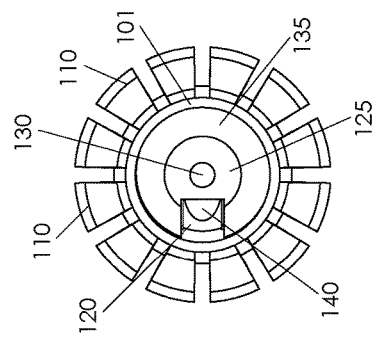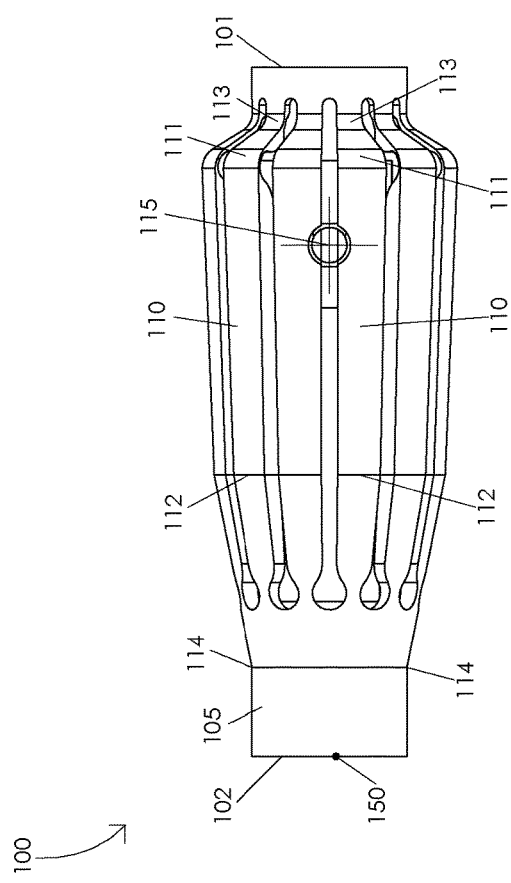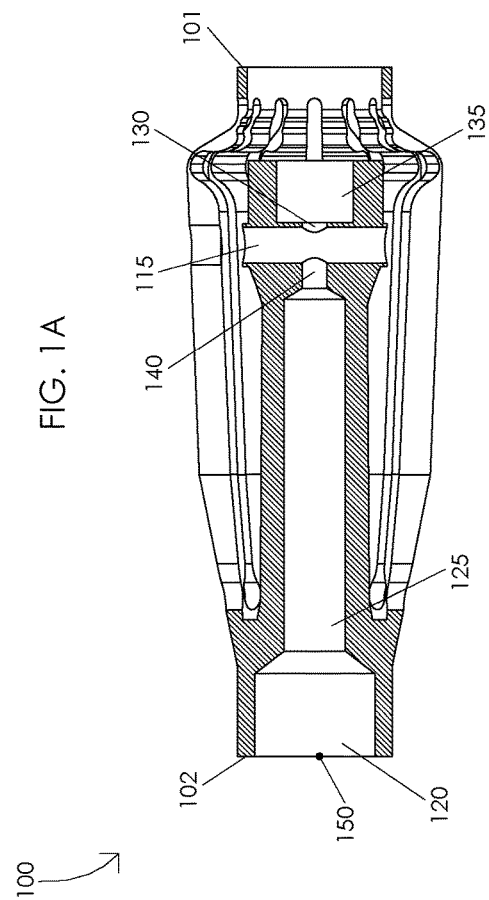

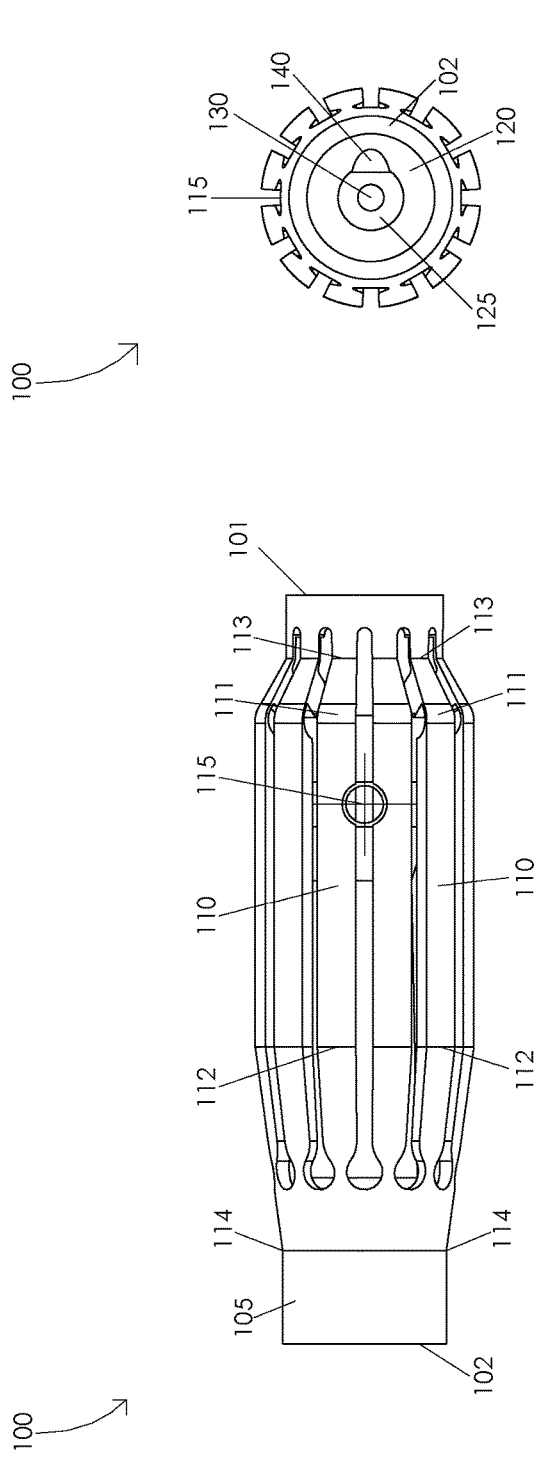
FIG. 1E
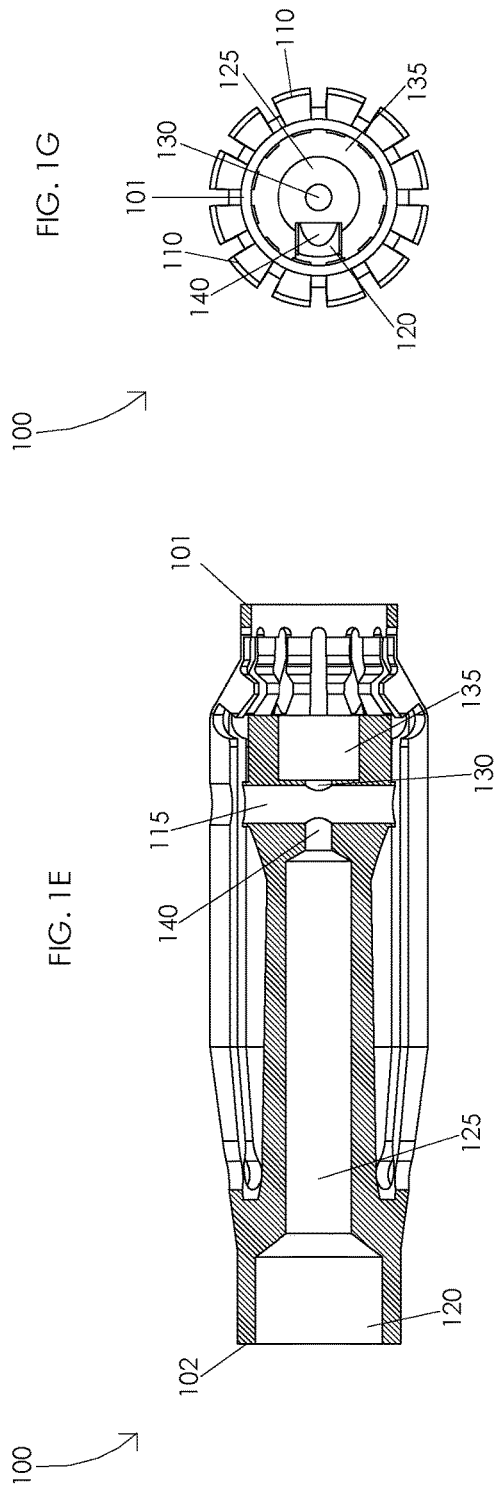
FIG. 1F
FIG. 1G
FIG. 1H

TOP

FRONT

TOP                    FRONT

TOP

FRONT

TOP    FRONT

US 10,413,445 B2

ATRAUMATIC MICROSURGICAL FORCEPS

CROSS-REFERENCE TO RELATED APPLICATIONS

This application is a continuation of prior application Ser. No. 14/953,307, filed Nov. 28, 2015.

FIELD OF THE INVENTION

The present disclosure relates to a surgical instrument, and, more particularly, to a microsurgical forceps.

BACKGROUND OF THE INVENTION

A microsurgical forceps may be used to perform a microsurgical procedure, e.g., an ophthalmic surgical procedure. For example, a surgeon may use a forceps to grasp and manipulate tissues or other surgical instruments to perform portions of a surgical procedure. A particular microsurgical procedure may require a surgeon to separate a first tissue from a second tissue without causing trauma to at least one of the tissues. Such a separation procedure may be particularly difficult for a surgeon to perform if the tissue surface geometry is not flat, e.g., if the tissue surface geometry is convex. For example, an ophthalmic surgeon may be required to remove an internal limiting membrane from a patient's retina without causing trauma to the patient's retina. Accordingly, there is a need for a microsurgical forceps that enables a surgeon to separate a first tissue from a second tissue without causing trauma to at least one of the tissues.

BRIEF SUMMARY OF THE INVENTION

The present disclosure presents an atraumatic microsurgical forceps. Illustratively, an atraumatic microsurgical forceps may comprise an actuation structure having an actuation structure distal end and an actuation structure proximal end, an actuation sleeve having an actuation sleeve distal end and an actuation sleeve proximal end, a surgical blank having a surgical blank distal end and a surgical blank proximal end, and atraumatic forceps jaws of the surgical blank having atraumatic forceps jaws distal ends and atraumatic forceps jaws proximal ends. In one or more embodiments, the surgical blank may be disposed within the actuation sleeve wherein at least a portion of the atraumatic forceps jaws extends from the actuation sleeve distal end. Illustratively, a compression of the actuation structure may be configured to gradually extend the actuation sleeve over the atraumatic forceps jaws proximal ends. In one or more embodiments, an extension of the actuation sleeve over the atraumatic forceps jaws proximal ends may be configured to gradually close the atraumatic forceps jaws wherein the atraumatic forceps jaws initially contact at the atraumatic forceps jaws distal ends.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A, 1B, 1C, 1D, 1E, 1F, 1G, and 1H are schematic diagrams illustrating an actuation structure;

DETAILED DESCRIPTION OF AN ILLUSTRATIVE EMBODIMENT

Figure 2:
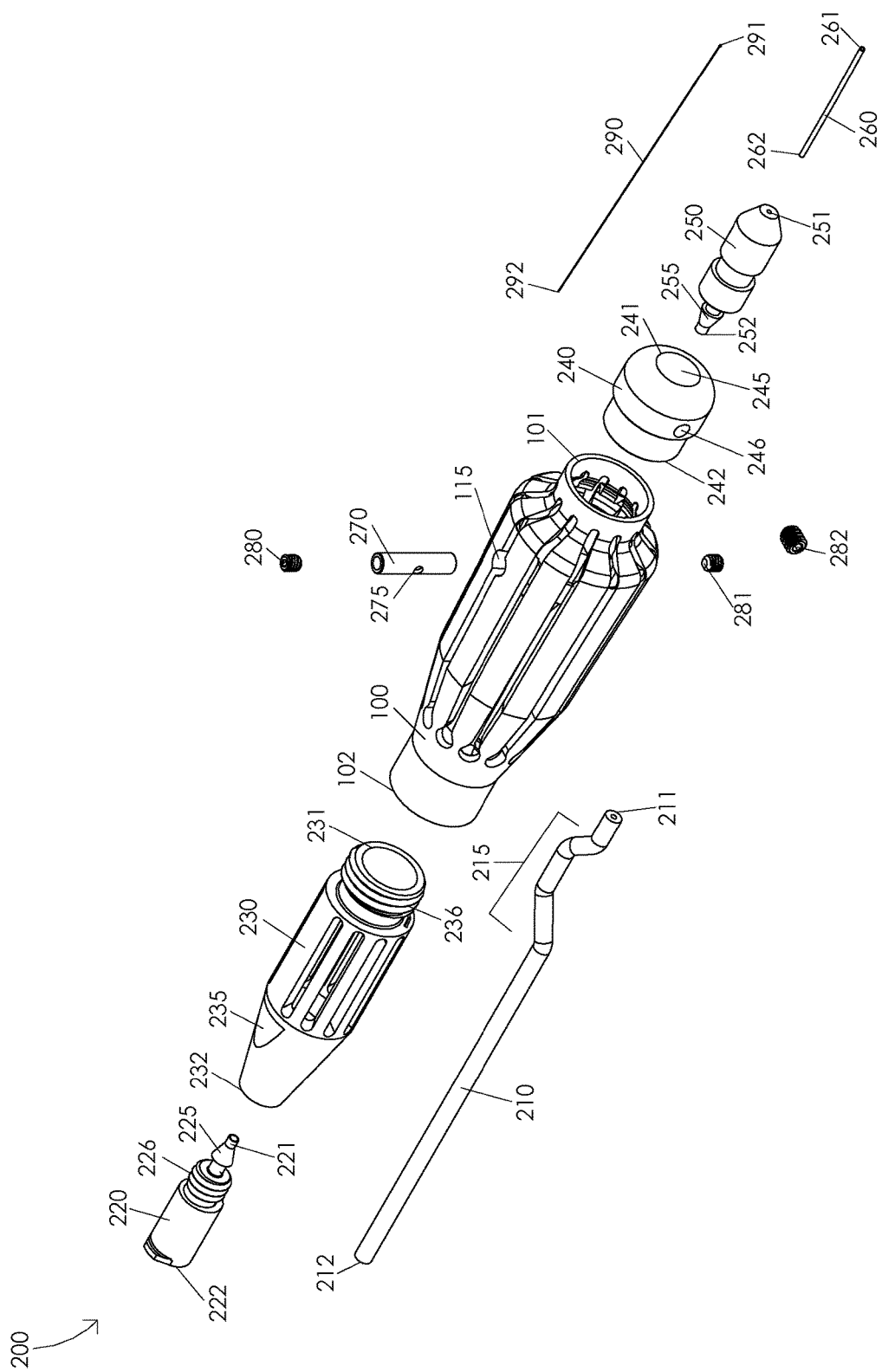
FIG. 2 is a schematic diagram illustrating an exploded view of a surgical instrument assembly.

FIGS. 1A, 1B, 1C, 1D, 1E, 1F, 1G, and 1H are schematic diagrams illustrating an actuation structure 100. FIG. 1A illustrates a top view of a decompressed actuation structure 100. Illustratively, actuation structure 100 may comprise an actuation structure distal end 101 and an actuation structure proximal end 102, an actuation structure base 105, a plurality of actuation arms 110, an actuation structure base interface 114, and a fixation mechanism housing 115. In one or more embodiments, each actuation arm 110 of a plurality of actuation arms 110 may comprise an extension joint 111, a distal extension mechanism 113, and a proximal extension mechanism 112. Illustratively, actuation structure distal end 101 may extend a decompressed distance from actuation structure proximal end 102, e.g., when actuation structure 100 comprises a decompressed actuation structure 100. In one or more embodiments, a decompressed distance may be a distance in a range of 1.6 to 3.0 inches, e.g., a decompressed distance may be 2.25 inches. Illustratively, a decompressed distance may be less than 1.6 inches or greater than 3.0 inches.

FIG. 1B illustrates a cross-sectional view of a decompressed actuation structure 100. Illustratively, actuation structure 100 may comprise a handle base housing 120, an inner bore 125, a surgical blank housing 130, an inner chamber 135, and an offset inner chamber 140. FIG. 1C illustrates a rear view of a decompressed actuation structure 100. FIG. 1D illustrates a front view of a decompressed actuation structure 100. In one or more embodiments, actuation structure 100 may be manufactured from any suitable material, e.g., polymers, metals, metal alloys, etc., or from any combination of suitable materials. Illustratively, actuation structure 100 may be manufactured from a shape memory material. In one or more embodiments, actuation structure 100 may be manufactured using a selective laser sintering machine. Illustratively, actuation structure 100 may be manufactured by additive manufacturing or 3D printing.

In one or more embodiments, actuation structure 100 may have a density in a range of 0.02 to 0.05 pounds per cubic inch, e.g., actuation structure 100 may have a density of 0.036 pounds per cubic inch. Illustratively, actuation structure 100 may have a density less than 0.02 pounds per cubic inch or greater than 0.05 pounds per cubic inch. In one or more embodiments, actuation structure 100 may have a mass in a range of 0.005 to 0.025 pounds, e.g., actuation structure 100 may have a mass of 0.013 pounds. Illustratively, actuation structure 100 may have a mass less than 0.005 pounds or greater than 0.025 pounds. In one or more embodiments, actuation structure 100 may have a volume in a range of 0.2 to 0.5 cubic inches, e.g., actuation structure 100 may have a volume of 0.365 cubic inches. Illustratively, actuation structure 100 may have a volume less than 0.2 cubic inches or greater than 0.5 cubic inches. In one or more embodiments, actuation structure 100 may have a surface area in a range of 10.0 to 15.0 square inches, e.g., actuation structure 100 may have a surface area of 13.25 square inches. Illustratively, actuation structure 100 may have a surface area less than 10.0 square inches or greater than 15.0 square inches. With respect to reference origin 150, actuation structure 100 may have a center of mass at X=1.15 inches, Y=−0.00083 inches, and Z=−0.0086 inches.

In one or more embodiments, actuation structure 100 may be manufactured from a material suitable for sterilization by a medical autoclave. Illustratively, actuation structure 100 may be manufactured from a material, e.g., Nylon, configured to withstand exposure to temperatures, pressures, and ambient conditions present in a medical autoclave without degradation. For example, actuation structure 100 may be configured to function normally after exposure in a temperature 250° F. for 15 minutes at an atmospheric pressure of 15 psi. In one or more embodiments, actuation structure 100 may be configured to be used in a surgical procedure and then sterilized by a medical autoclave at least three times. Illustratively, actuation structure 100 may be configured to be used in a surgical procedure and then sterilized by a medical autoclave more than three times.

FIG. 1E illustrates a top view of a compressed actuation structure 100. FIG. 1F illustrates a cross-sectional view of a compressed actuation structure 100. FIG. 1G illustrates a rear view of a compressed actuation structure 100. FIG. 1H illustrates a front view of a compressed actuation structure 100. In one or more embodiments, actuation structure 100 may be configured to project actuation structure distal end 101 a first distance from actuation structure proximal end 102, e.g., when actuation structure 100 is fully decompressed. Illustratively, actuation structure 100 may comprise a shape memory material configured to project actuation structure distal end 101 a second distance from actuation structure proximal end 102, e.g., when actuation structure 100 is fully compressed. In one or more embodiments, the second distance from actuation structure proximal end 102 may be greater than the first distance from actuation structure proximal end 102. Illustratively, a compression of actuation structure 100 may be configured to gradually extend actuation structure distal end 101 relative to actuation structure proximal end 102.

In one or more embodiments, actuation structure distal end 101 may extend a compressed distance from actuation structure proximal end 102, e.g., when actuation structure 100 comprises a compressed actuation structure 100. Illustratively, a compressed distance may be a distance in a range of 1.6 to 3.0 inches, e.g., a compressed distance may be 2.26 inches. In one or more embodiments, a compressed distance may be less than 1.6 inches or greater than 3.0 inches. Illustratively, a compressed distance may be a range of 0.005 to 0.05 inches greater than a decompressed distance. In one or more embodiments, a compressed distance may be less than 0.005 inches greater than a decompressed distance. Illustratively, a compressed distance may be greater than 0.05 inches greater than a decompressed distance. In one or more embodiments, a compressed distance may be in a range of 0.25 to 1.0 percent greater than a decompressed distance. Illustratively, a compressed distance may be less than 0.25 percent greater than a decompressed distance. In one or more embodiments, a compressed distance may be more than 1.0 percent greater than a decompressed distance.

Illustratively, actuation structure 100 may be compressed by an application of a force, e.g., a compressive force, to a portion of actuation structure 100. In one or more embodiments, an application of a compressive force in a range of 0.2 to 1.0 pounds may compress actuation structure 100, e.g., an application of a compressive force of 0.84 pounds may be configured to compress actuation structure 100. Illustratively, an application of a compressive force of less than 0.2 pounds or greater than 1.0 pounds may be configured to compress actuation structure 100. In one or more embodiments, actuation structure 100 may be compressed by an application of one or more compressive forces at one or more locations around an outer perimeter of actuation structure 100. Illustratively, the one or more locations may comprise any particular locations of a plurality of locations around an outer perimeter of actuation structure 100. For example, a surgeon may compress actuation structure 100 by squeezing actuation structure 100. Illustratively, a surgeon may compress actuation structure 100 by squeezing actuation structure 100 at any particular location of a plurality of locations around an outer perimeter of actuation structure 100.

In one or more embodiments, a surgeon may compress actuation structure 100 by applying a force to a portion of actuation structure 100, e.g., when actuation structure 100 is in a first rotational orientation. Illustratively, the surgeon may then rotate actuation structure 100 and compress actuation structure 100 by applying a force to a portion of actuation structure 100, e.g., when actuation structure 100 is in a second rotational orientation. In one or more embodiments, the surgeon may then rotate actuation structure 100 and compress actuation structure 100 by applying a force to a portion of actuation structure, e.g., when actuation structure 100 is in a third rotational orientation. Illustratively, a surgeon may compress actuation structure 100 by applying a force to a portion of actuation structure 100, e.g., when actuation structure 100 is in any rotational orientation.

In one or more embodiments, actuation structure 100 may be compressed by an application of a compressive force to any one or more actuation arms 110 of a plurality of actuation arms 110. Illustratively, each actuation arm 110 may be connected to one or more actuation arms 110 of a plurality of actuation arms 110 wherein an actuation of a particular actuation arm 110 may be configured to actuate every actuation arm 110 of a plurality of actuation arms 110. In one or more embodiments, one or more actuation arms 110 may be configured to actuate in pairs or groups. For example, an actuation of a first actuation arm 110 may be configured to actuate a second actuation arm 110.

Illustratively, a compression of actuation structure 100, e.g., due to an application of a force to a portion of actuation structure 100, may be configured to expand one or more extension joints 111 of a particular actuation arm 110. In one or more embodiments, an expansion of an extension joint 111 of a particular actuation arm 110 may be configured to increase a distance between a distal end and a proximal end of the particular actuation arm 110. Illustratively, an expansion of an extension joint 111 of a particular actuation arm 110 may be configured to expand an extension joint 111 of every actuation arm 110 of a plurality of actuation arms 110. In one or more embodiments, an expansion of an extension joint 111 of every actuation arm 110 of a plurality of actuation arms 110 may be configured to increase a distance between actuation structure distal end 101 and actuation structure proximal end 102.

Illustratively, a decompression of actuation structure 100, e.g., due to a reduction of a force applied to a portion of actuation structure 100, may be configured to collapse one or more extension joints 111 of a particular actuation arm 110. In one or more embodiments, a collapse of an extension joint 111 of a particular actuation arm 110 may be configured to decrease a distance between a distal end and a proximal end of the particular actuation arm 110. Illustratively, a collapse of an extension joint 111 of a particular actuation arm 110 may be configured to collapse an extension joint 111 of every actuation arm 110 of a plurality of actuation arms 110. In one or more embodiments, a collapse of an extension joint 111 of every actuation arm 110 of a plurality of actuation arms 110 may be configured to decrease a distance between actuation structure distal end 101 and actuation structure proximal end 102.

Illustratively, a compression of actuation structure 100, e.g., due to an application of a force to a portion of actuation structure 100, may be configured to extend a proximal extension mechanism 112 of a particular actuation arm 110. In one or more embodiments, an extension of a proximal extension mechanism 112 of a particular actuation arm 110 may be configured to increase a distance between a distal end and a proximal end of the particular actuation arm 110. Illustratively, an extension of a proximal extension mechanism 112 of a particular actuation arm 110 may be configured to extend a proximal extension mechanism 112 of every actuation arm 110 of a plurality of actuation arms 110. In one or more embodiments, an extension of a proximal extension mechanism 112 of every actuation arm 110 of a plurality of actuation arms 110 may be configured to increase a distance between actuation structure distal end 101 and actuation structure proximal end 102.

Illustratively, a decompression of actuation structure 100, e.g., due to a reduction of a force applied to a portion of actuation structure 100, may be configured to retract a proximal extension mechanism 112 of a particular actuation arm 110. In one or more embodiments, a retraction of a proximal extension mechanism 112 of a particular actuation arm 110 may be configured to decrease a distance between a distal end and a proxies mal end of the particular actuation arm 110. Illustratively, a retraction of a proximal extension mechanism 112 of a particular actuation arm 110 may be configured to retract a proximal extension mechanism 112 of every actuation arm 110 of a plurality of actuation arms 110. In one or more embodiments, a retraction of a proximal extension mechanism 112 of every actuation arm 110 of a plurality of actuation arms 110 may be configured to decrease a distance between actuation structure distal end 101 and actuation structure proximal end 102.

Illustratively, a compression of actuation structure 100, e.g., due to an application of a force to a portion of actuation structure 100, may be configured to extend a distal extension mechanism 113 of a particular actuation arm 110. In one or more embodiments, an extension of a distal extension mechanism 113 of a particular actuation arm 110 may be configured to increase a distance between a distal end and a proximal end of the particular actuation arm 110. Illustratively, an extension of a distal extension mechanism 113 of a particular actuation arm 110 may be configured to extend a distal extension mechanism 113 of every actuation arm 110 of a plurality of actuation arms 110. In one or more embodiments, an extension of a distal extension mechanism 113 of every actuation arm 110 of a plurality of actuation arms 110 may be configured to increase a distance between actuation structure distal end 101 and actuation structure proximal end 102.

Illustratively, a decompression of actuation structure 100, e.g., due to a reduction of a force applied to a portion of actuation structure 100, may be configured to retract a distal extension mechanism 113 of a particular actuation arm 110. In one or more embodiments, a retraction of a distal extension mechanism 113 of a particular actuation arm 110 may be configured to decrease a distance between a distal end and a proximal end of the particular actuation arm 110. Illustratively, a retraction of a distal extension mechanism 113 of a particular actuation arm 110 may be configured to retract a distal extension mechanism 113 of every actuation arm 110 of a plurality of actuation arms 110. In one or more embodiments, a retraction of a distal extension mechanism 113 of every actuation arm 110 of a plurality of actuation arms 110 may be configured to decrease a distance between actuation structure distal end 101 and actuation structure proximal end 102.

Illustratively, a compression of actuation structure 100, e.g., due to an application of a force to a portion of actuation structure 100, may be configured to extend an extension joint 111, a proximal extension mechanism 112, and a distal extension mechanism 113 of a particular actuation arm 110. In one or more embodiments, an extension of an extension joint 111, a proximal extension mechanism 112, and a distal extension mechanism 113 of a particular actuation arm 110 may be configured to increase a distance between a distal end and a proximal end of the particular actuation arm 110. Illustratively, an extension of an extension joint 111, a proximal extension mechanism 112, and a distal extension mechanism 113 of a particular actuation arm 110 may be configured to extend an extension joint 111, a proximal extension mechanism 112, and a distal extension mechanism 113 of every actuation arm 110 of a plurality of actuation arms 110. In one or more embodiments, an extension of an extension joint 111, a proximal extension mechanism 112, and a distal extension mechanism 113 of every actuation arm 110 of a plurality of actuation arms 110 may be configured to increase a distance between actuation structure distal end 101 and actuation structure proximal end 102.

Illustratively, a decompression of actuation structure 100, e.g., due to a reduction of a force applied to a portion of actuation structure 100, may be configured to retract an extension joint 111, a proximal extension mechanism 112, and a distal extension mechanism 113 of a particular actuation arm 110. In one or more embodiments, a retraction of an extension joint 111, a proximal extension mechanism 112, and a distal extension mechanism 113 of a particular actuation arm 110 may be configured to decrease a distance between a distal end and a proximal end of the particular actuation arm 110. Illustratively, a retraction of an extension joint 111, a proximal extension mechanism 112, and a distal extension mechanism 113 of a particular actuation arm 110 may be configured to retract an extension joint 111, a proximal extension mechanism 112, and a distal extension mechanism 113 of every actuation arm 110 of a plurality of actuation arms 110. In one or more embodiments, a retraction of an extension joint 111, a proximal extension mechanism 112, and a distal extension mechanism 113 of every actuation arm 110 of a plurality of actuation arms 110 may be configured to decrease a distance between actuation structure distal end 101 and actuation structure proximal end 102.

FIG. 2 is a schematic diagram illustrating an exploded view of a surgical instrument assembly 200. Illustratively, a surgical instrument assembly may comprise a tube 210 having a tube distal end 211 and a tube proximal end 212, an end plug 220 having an end plug distal end 221 and an end plug proximal end 222, a handle base 230 having a handle base distal end 231 and a handle base proximal end 232, an actuation structure 100 having an actuation structure distal end 101 and an actuation structure proximal end 102, an outer nosecone 240 having an outer nosecone distal end 241 and an outer nosecone proximal end 242, an inner nosecone 250 having an inner nosecone distal end 251 an inner nosecone proximal end 252, an actuation sleeve 260 having an actuation sleeve distal end 261 and an actuation sleeve proximal end 262, a wire lock 270, a first fixation mechanism 280, a second fixation mechanism 281, a nosecone fixation mechanism 282, and a surgical blank 290 having a surgical blank distal end 291 and a surgical blank proximal end 292. In one or more embodiments, tube 210 may comprise a tube curved portion 215. Illustratively, tube curved portion 215 may be configured to curve tube 210 around wire lock 270.

In one or more embodiments, tube 210 may be manufactured from a material suitable for sterilization by a medical autoclave. Illustratively, tube 210 may be manufactured from a material configured to withstand exposure to temperatures, pressures, and ambient conditions present in a medical autoclave without degradation. For example, tube 210 may be configured to function normally after exposure in a temperature 250° F. for 15 minutes at an atmospheric pressure of 15 psi. In one or more embodiments, tube 210 may be configured to be used in a surgical procedure and then sterilized by a medical autoclave at least three times. Illustratively, tube 210 may be configured to be used in a surgical procedure and then sterilized by a medical autoclave more than three times.

In one or more embodiments, end plug 220 may comprise an end plug thread 226 and a proximal barb fitting 225. Illustratively, end plug 220 may comprise a lure hub. For example, end plug 220 may comprise an inner bore aligned with an inner bore of proximal barb fitting 225. In one or more embodiments, proximal barb fitting 225 may be configured to interface with tube proximal end 212. Illustratively, a portion of end plug 220 may be disposed within handle base 230, e.g., end plug distal end 221 may be disposed within handle base 230. In one or more embodiments, a portion of end plug 220 may be fixed within handle base 230, e.g., by an adhesive or any suitable fixation means. Illustratively, a portion of end plug 220 may be fixed within handle base 230, e.g., a portion of handle base 230 may comprise a thread configured to match end plug thread 226 and end plug 220 may be screwed into handle base 230. In one or more embodiments, a portion of end plug 220 may be fixed within handle base 230 by a press fit, a setscrew, etc. Illustratively, end plug 220 and handle base 230 may comprise a single unit. In one or more embodiments, end plug 220 may be manufactured from any suitable material, e.g., polymers, metals, metal alloys, etc., or from any combination of suitable materials.

In one or more embodiments, end plug 220 may be manufactured from a material suitable for sterilization by a medical autoclave. Illustratively, end plug 220 may be manufactured from a material configured to withstand exposure to temperatures, pressures, and ambient conditions present in a medical autoclave without degradation. For example, end plug 220 may be configured to function normally after exposure in a temperature 250° F. for 15 minutes at an atmospheric pressure of 15 psi. In one or more embodiments, end plug 220 may be configured to be used in a surgical procedure and then sterilized by a medical autoclave at least three times. Illustratively, end plug 220 may be configured to be used in a surgical procedure and then sterilized by a medical autoclave more than three times.

Illustratively, handle base 230 may comprise an assembly grip point 235 and a handle base thread 236. In one or more embodiments, a portion of handle base 230 may be disposed within actuation structure 100, e.g., handle base distal end 231 may be disposed within handle base housing 120. Illustratively, a portion of handle base 230 may be fixed within actuation structure 100, e.g., by an adhesive or any suitable fixation means. In one or more embodiments, a portion of handle base 230 may be fixed within a portion of actuation structure 100, e.g., a portion of actuation structure 100 may comprise a thread configured to match handle base thread 236 and handle base 230 may be screwed into actuation structure 100. Illustratively, assembly grip point 235 may be configured to facilitate a fixation of a portion of handle base 230 within actuation structure 100, e.g., assembly grip point 235 may be configured to facilitate a screwing of handle base into actuation structure. In one or more embodiments, a portion of handle base 230 may be fixed within actuation structure 100 by a press fit, a setscrew, etc. Illustratively, handle base 230 and actuation structure 100 may comprise a single unit. For example, end plug 220, handle base 230, and actuation structure 100 may comprise a single unit. In one or more embodiments, handle base 230 may be manufactured from any suitable material, e.g., polymers, metals, metal alloys, etc., or from any combination of suitable materials.

In one or more embodiments, handle base 230 may be manufactured from a material suitable for sterilization by a medical autoclave. Illustratively, handle base 230 may be manufactured from a material configured to withstand exposure to temperatures, pressures, and ambient conditions present in a medical autoclave without degradation. For example, handle base 230 may be configured to function normally after exposure in a temperature 250° F. for 15 minutes at an atmospheric pressure of 15 psi. In one or more embodiments, handle base 230 may be configured to be used in a surgical procedure and then sterilized by a medical autoclave at least three times. Illustratively, handle base 230 may be configured to be used in a surgical procedure and then sterilized by a medical autoclave more than three times.

Illustratively, outer nosecone 240 may comprise an outer nosecone inner chamber 245 and a nosecone fixation mechanism housing 246. In one or more embodiments, inner nosecone 250 may comprise a distal barb fitting 255. For example, inner nosecone 250 may comprise an inner bore aligned with an inner bore of distal barb fitting 255. Illustratively, distal barb fitting 255 may be configured to interface with tube distal end 211. In one or more embodiments, a portion of inner nosecone 250 may be disposed within outer nosecone inner chamber 245, e.g., inner nosecone proximal end 252 may be disposed within outer nosecone inner chamber 245. Illustratively, inner nosecone 250 may be fixed within outer nosecone inner chamber 245, e.g., by an adhesive or any suitable fixation means. In one or more embodiments, nosecone fixation mechanism 282 may be configured to fix inner nosecone 250 to outer nosecone 240. Illustratively, nosecone fixation mechanism 282 may be disposed within nosecone fixation mechanism housing 246. In one or more embodiments, a portion of inner nosecone 250 may be fixed to a portion of nosecone fixation mechanism 282, e.g., by an adhesive or any suitable fixation means. Illustratively, nosecone fixation mechanism 282 may comprise a setscrew configured to fix inner nosecone 250 to outer nosecone 240, e.g., by a press fit or any suitable fixation means. In one or more embodiments, inner nosecone 250 and outer nosecone 240 may comprise a single unit. Illustratively, inner nosecone 250 and outer nosecone 240 may be manufactured from any suitable material, e.g., polymers, metals, metal alloys, etc., or from any combination of suitable materials.

In one or more embodiments, a portion of outer nosecone 240 may be fixed to actuation structure 100, e.g., outer nosecone proximal end 242 may be fixed to actuation structure distal end 101. Illustratively, a portion of outer nosecone 240 may be fixed to actuation structure 100, e.g., by an adhesive or any suitable fixation means. In one or more embodiments, a portion of outer nosecone 240 may be disposed within a portion of actuation structure 100, e.g., outer nosecone proximal end 242 may be disposed within a portion of actuation structure 100. Illustratively, a portion of outer nosecone 240 may be fixed within a portion of actuation structure 100, e.g., by an adhesive or any suitable fixation means.

In one or more embodiments, a portion of actuation sleeve 260 may be fixed to a portion of inner nosecone 250, e.g., actuation sleeve proximal end 262 may be fixed to inner nosecone distal end 251. Illustratively, a portion of actuation sleeve 260 may be fixed to a portion of inner nosecone 250, e.g., by an adhesive or any suitable fixation means. In one or more embodiments, a portion of actuation sleeve 260 may be disposed within a portion of inner nosecone 250, e.g., actuation sleeve proximal end 262 may be disposed within inner nosecone 250. Illustratively, a portion of actuation sleeve 260 may be fixed within inner nosecone 250, e.g., by an adhesive or any suitable fixation means. In one or more embodiments, a portion of actuation sleeve 260 may be fixed within inner nosecone 250, e.g., by a press fit, a setscrew, etc. Illustratively, actuation sleeve 260 may be manufactured from any suitable material, e.g., polymers, metals, metal alloys, etc., or from any combination of suitable materials.

In one or more embodiments, tube proximal end 212 may interface with proximal barb 225. Illustratively, a portion of tube 210 may be configured to fit over a portion of proximal barb 225, e.g., to form a hermetic seal. In one or more embodiments, tube 210 may be disposed within handle base 230, handle base housing 120, inner bore 125, offset inner chamber 140, inner chamber 135, and outer nosecone 240. Illustratively, tube 210 may be disposed with actuation structure 100 wherein tube curved portion 215 may be disposed in offset inner chamber 140. In one or more embodiments, tube distal end 211 may interface with distal barb 255. Illustratively, a portion of tube 210 may be configured to fit over a portion of distal barb 255, e.g., to form a hermetic seal.

In one or more embodiments, wire lock 270 may be disposed within fixation mechanism housing 115. Illustratively, wire lock 270 may be fixed within fixation mechanism housing 115, e.g., by an adhesive or any suitable fixation means. In one or more embodiments, surgical blank 290 may be disposed within actuation structure 100 and actuation sleeve 260. Illustratively, surgical blank 290 may be disposed within wire lock 270, wire lock interface 275, surgical blank housing 130, inner chamber 135, outer nosecone 240, inner nosecone 250, and actuation sleeve 260. In one or more embodiments, a portion of surgical blank 290 may extend from actuation sleeve distal end 261. Illustratively, surgical blank distal end 291 may extend from actuation sleeve distal end 261. In one or more embodiments, surgical blank 290 may be fixed within wire lock 270, e.g., by an adhesive or any suitable fixation means. Illustratively, first fixation mechanism 280 and second fixation mechanism 281 may be configured to fix a portion of surgical blank 290 within wire lock 270, e.g., first fixation mechanism 280 and second fixation mechanism 281 may be disposed within wire lock 270. In one or more embodiments, first fixation mechanism 280 and second fixation mechanism 281 may comprise setscrews configured to firmly fix a portion of surgical blank 290 within wire lock 270.

Figure 3:
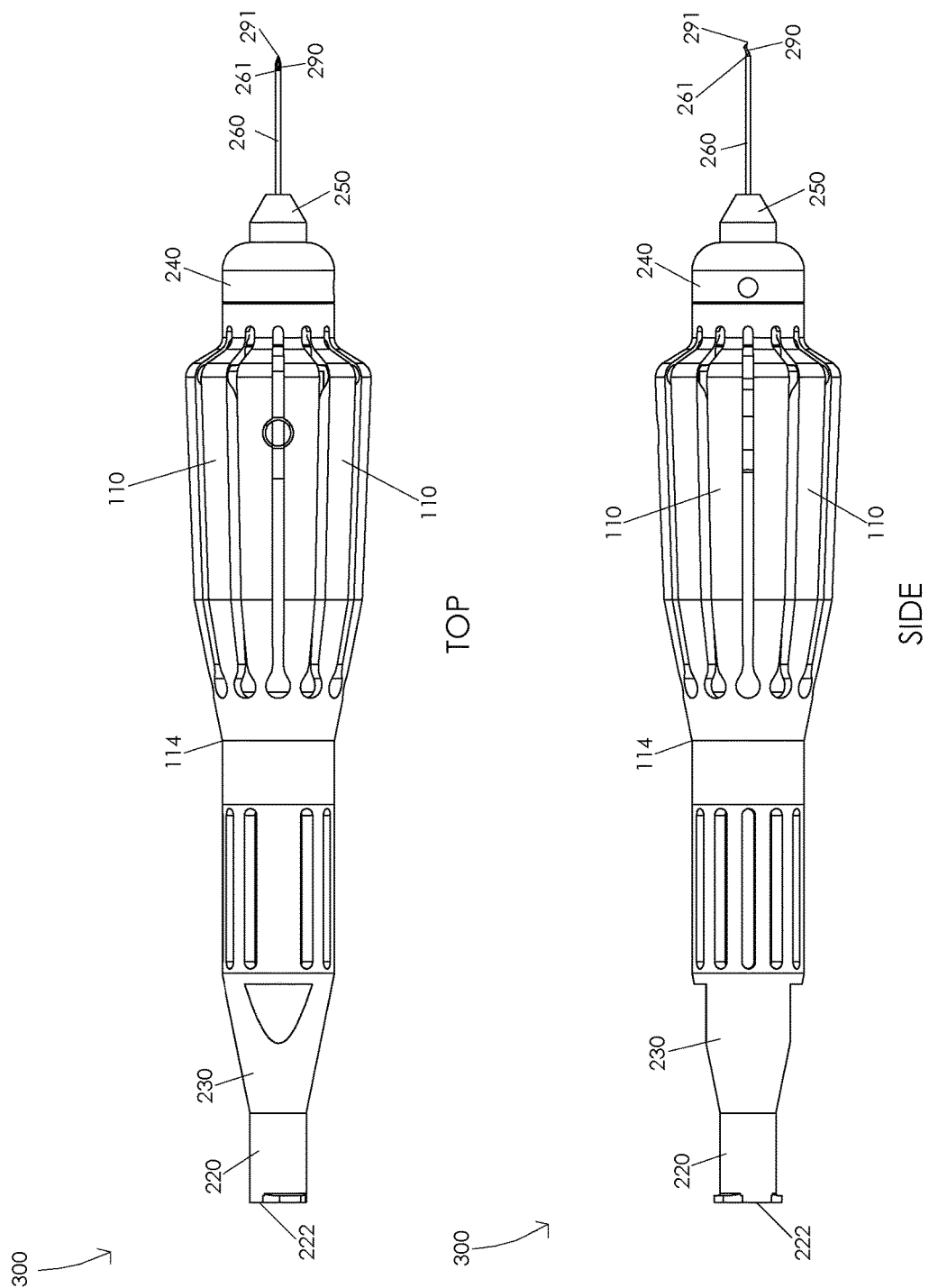
FIG. 3 is a schematic diagram illustrating a surgical instrument.

FIG. 3 is a schematic diagram illustrating a surgical instrument 300. FIG. 3 illustrates a top view and a side view of surgical instrument 300. Illustratively, a compression of actuation structure 100 may be configured to extend actuation structure distal end 101 relative to actuation structure proximal end 102, e.g., a compression of actuation structure 100 may be configured to increase a distance between actuation structure distal end 101 and actuation structure proximal end 102. In one or more embodiments, an extension of actuation structure distal end 101 relative to actuation structure proximal end 102 may be configured to extend outer nosecone 240 relative to handle base 230. Illustratively, an extension of outer nosecone 240 relative to handle base 230 may be configured to extend inner nosecone 250 relative to surgical blank 290. In one or more embodiments, an extension of inner nosecone 250 relative to surgical blank 290 may be configured to extend actuation sleeve 260 relative to surgical blank 290.

Illustratively, a decompression of actuation structure 100 may be configured to retract actuation structure distal end 101 relative to actuation structure proximal end 102, e.g., a decompression of actuation structure 100 may be configured to reduce a distance between actuation structure distal end 101 and actuation structure proximal end 102. In one or more embodiments, a retraction of actuation structure distal end 101 relative to actuation structure proximal end 102 may be configured to retract outer nosecone 240 relative to handle base 230. Illustratively, a retraction of outer nosecone 240 relative to handle base 230 may be configured to retract inner nosecone 250 relative to surgical blank 290. In one or more embodiments, a retraction of inner nosecone 250 relative to surgical blank 290 may be configured to retract actuation sleeve 260 relative to surgical blank 290.

Figure 4:
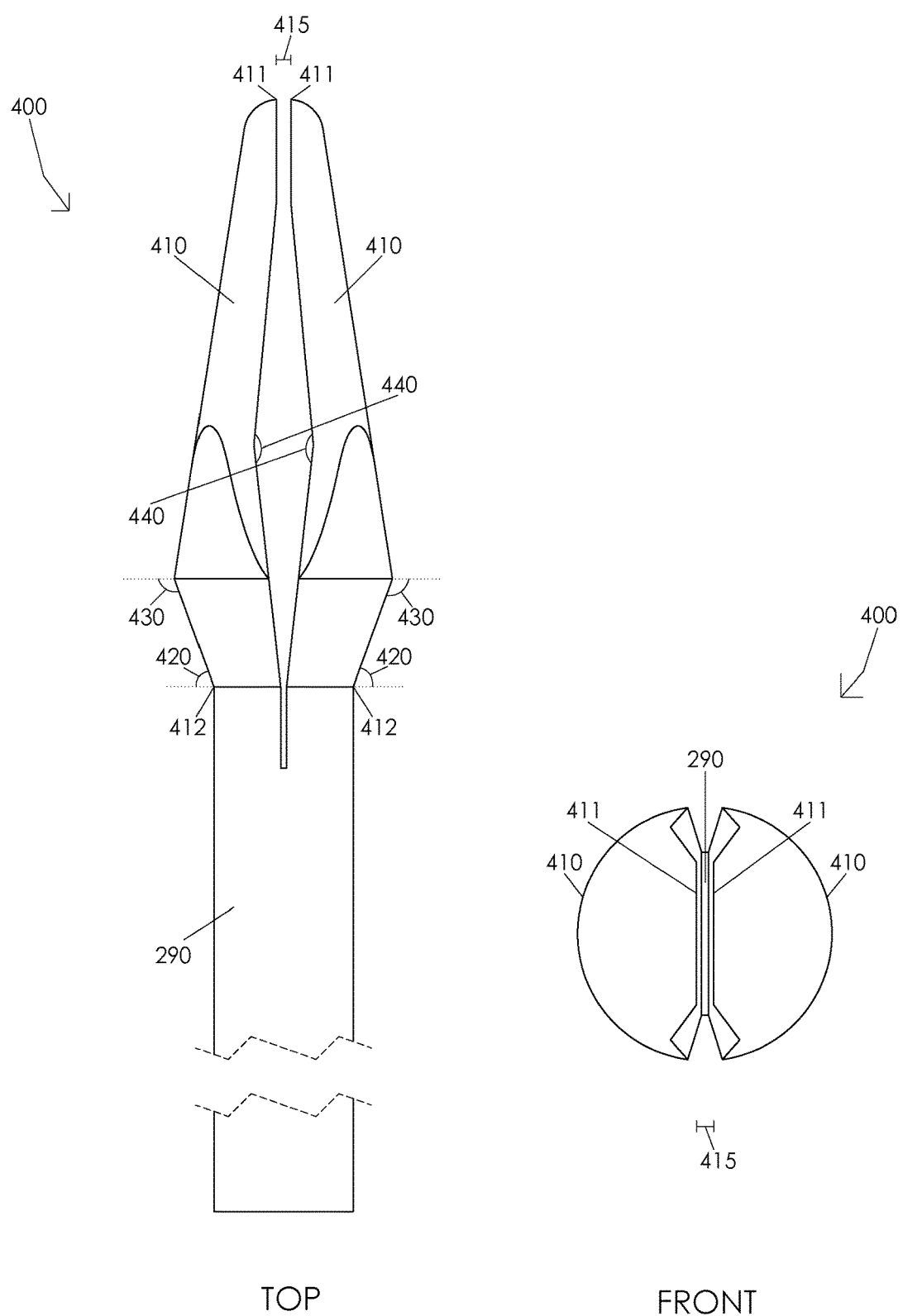
FIG. 4 is a schematic diagram illustrating an atraumatic forceps.

FIG. 4 is a schematic diagram illustrating an atraumatic forceps 400. FIG. 4 illustrates a top view and a front view of an atraumatic forceps 400. Illustratively, atraumatic forceps 400 may be manufactured with dimensions configured for performing microsurgical procedures, e.g., ophthalmic surgical procedures. In one or more embodiments, atraumatic forceps 400 may be manufactured from surgical blank 290. Illustratively, atraumatic forceps 400 may be manufactured by modifying surgical blank 290, e.g., with an electric discharge machine. In one or more embodiments, atraumatic forceps 400 may be manufactured by modifying surgical blank 290, e.g., with a laser, a file, or any suitable modification means. Illustratively, atraumatic forceps 400 may comprise a plurality of atraumatic forceps jaws 410, a first contour angle 420, a second contour angle 430, and a third contour angle 440.

Illustratively, each atraumatic forceps jaw 410 of a plurality of atraumatic forceps jaws 410 may comprise an atraumatic forceps jaw distal end 411 and an atraumatic forceps jaw proximal end 412. In one or more embodiments, a first atraumatic forceps jaw distal end 411 and a second atraumatic forceps jaw distal end 411 may be separated by a distance 415. Illustratively, distance 415 may comprise a distance in a range of 0.005 to 0.08 inches, e.g., distance 415 may comprise a distance of 0.04 inches. In one or more embodiments, distance 415 may comprise a distance less than 0.005 inches or greater than 0.08 inches. Illustratively, atraumatic forceps 400 may be configured to separate a first tissue from a surface of a second tissue without damaging the second tissue. For example, atraumatic forceps 400 may be configured to separate a first tissue having a convex surface geometry from a second tissue having a convex surface geometry without damaging the second tissue. In one or more embodiments, the first tissue may comprise an internal limiting membrane and the second tissue may comprise a retina. Illustratively, distance 415 may comprise a distance in a range of 200 to 600 times an average thickness of the first tissue, e.g., distance 415 may comprise a distance 291 times the average thickness of the first tissue. In one or more embodiments, distance 415 may comprise a distance less than 200 times or greater than 600 times the average thickness of the first tissue. Illustratively, distance 415 may comprise a distance in a range of 200 to 600 times an average thickness of an internal limiting membrane, e.g., distance 415 may comprise a distance 291 times the average thickness of an internal limiting membrane. In one or more embodiments, distance 415 may comprise a distance less than 200 times or greater than 600 times the average thickness of an internal limiting membrane.

Illustratively, first contour angle 420 may comprise any angle less than 90 degrees, e.g., first contour angle 420 may comprise an angle in a range of 60 to 80 degrees. In one or more embodiments, first contour angle 420 may comprise an angle less than 60 degrees or greater than 80 degrees. Illustratively, first contour angle 420 may comprise a 70 degree angle. In one or more embodiments, second contour angle 430 may comprise any angle greater than 90 degrees, e.g., second contour angle 430 may comprise an angle in a range of 100 to 120 degrees. Illustratively, second contour angle 430 may comprise an angle less than 100 degrees or greater than 120 degrees. In one or more embodiments, second contour angle 430 may comprise a 110 degree angle. Illustratively, third contour angle 440 may comprise any angle greater than 90 degrees, e.g., third contour angle 440 may comprise an angle in a range of 160 to 175 degrees. In one or more embodiments, third contour angle 440 may comprise an angle less than 160 degrees or greater than 175 degrees. Illustratively, third contour angle 440 may comprise a 168 degree angle.

In one or more embodiments, atraumatic forceps jaws 410 may be configured to close at atraumatic forceps jaws distal ends 411 as actuation sleeve 260 is gradually actuated over atraumatic forceps jaws proximal ends 412. Illustratively, an extension of actuation sleeve 260 relative to surgical blank 290 may be configured to decrease a distance 415 between a first atraumatic forceps jaw distal end 411 and a second atraumatic forceps jaw distal end 411. In one or more embodiments, an extension of actuation sleeve 260 over a first atraumatic forceps jaw proximal end 412 and a second atraumatic forceps jaw proximal end 412 may be configured to cause the first atraumatic forceps jaw distal end 411 and the second atraumatic forceps jaw distal end 411 to contact before any other portion of the first atraumatic forceps jaw 410 contacts any other portion of the second atraumatic forceps jaw 410.

Figure 5A:
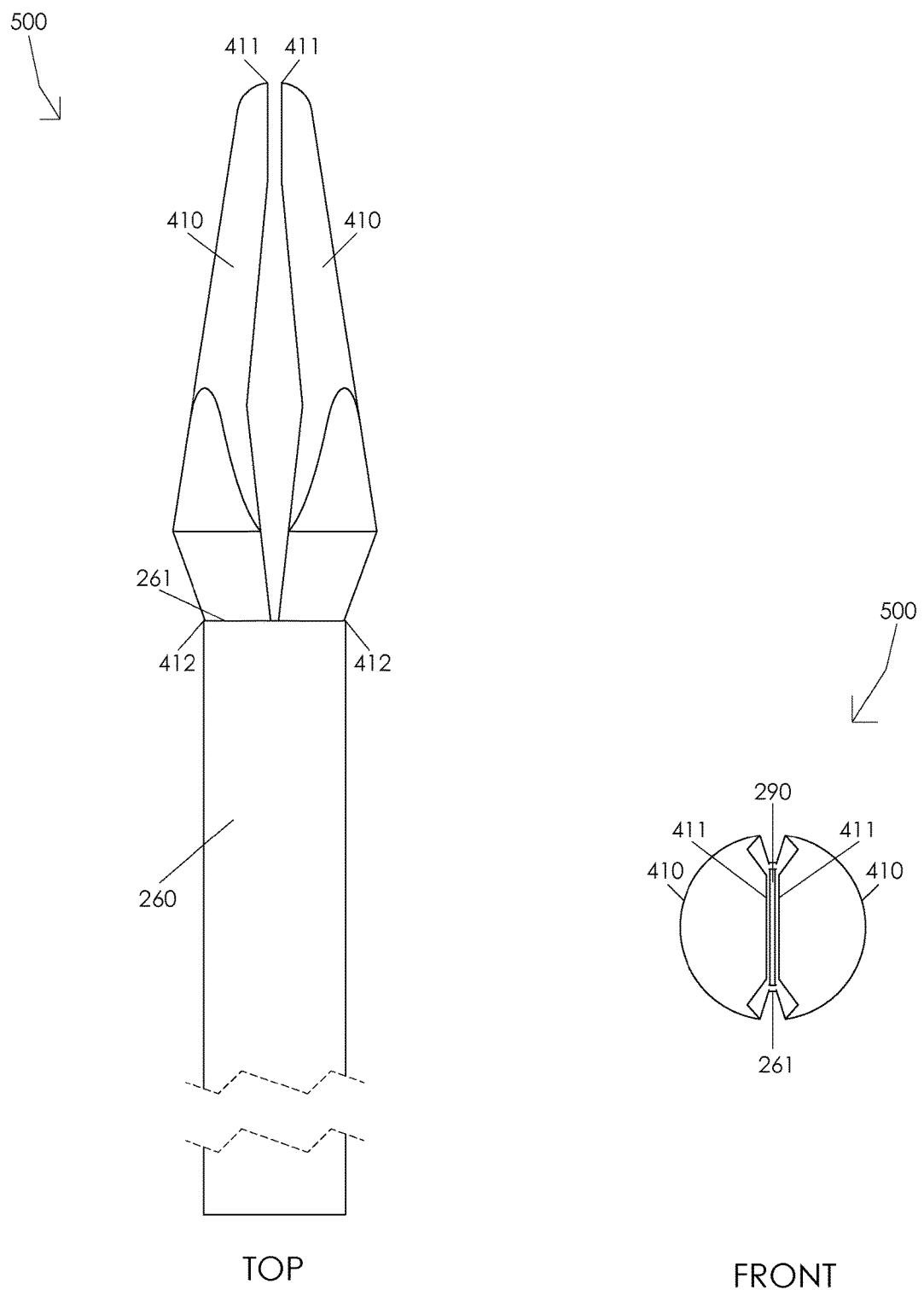
FIGS. 5A, 5B, and 5C are schematic diagrams illustrating a gradual closing of an atraumatic forceps.
Figure 5B:
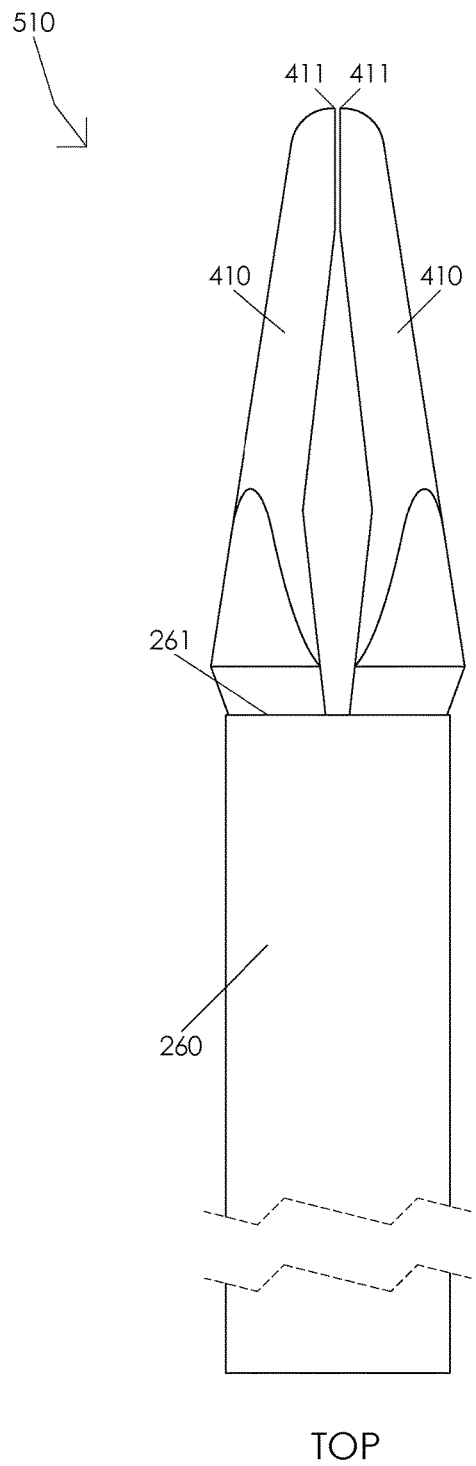
Figure 5B:
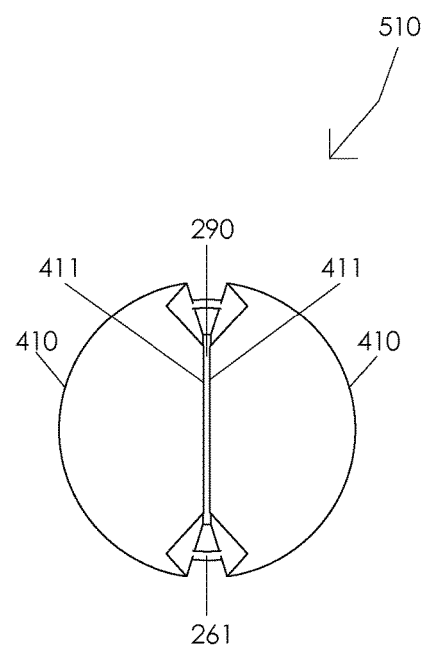
Figure 5C:
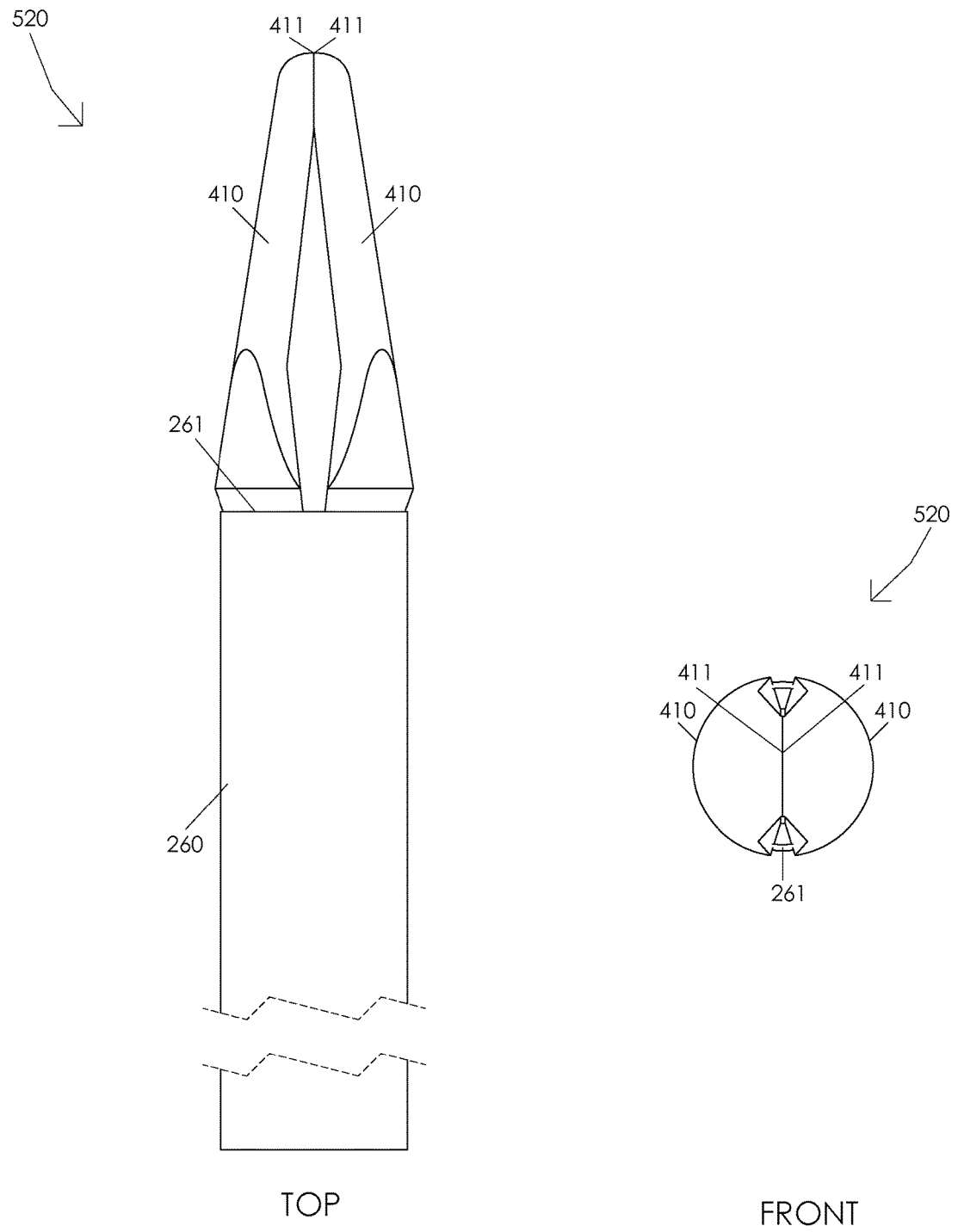

FIGS. 5A, 5B, and 5C are schematic diagrams illustrating a gradual closing of an atraumatic forceps 400. FIG. 5A illustrates a top view and a front view of an open atraumatic forceps 500. In one or more embodiments, atraumatic forceps 400 may comprise an open atraumatic forceps 500, e.g., when a first atraumatic forceps jaw distal end 411 is separated from a second atraumatic forceps jaw distal end 411 by distance 415. Illustratively, atraumatic forceps 400 may comprise an open atraumatic forceps 500, e.g., when actuation sleeve 260 is fully retracted relative to atraumatic forceps jaws proximal ends 412. Illustratively, atraumatic forceps 400 may comprise an open atraumatic forceps 500, e.g., when actuation structure 100 is fully decompressed.

FIG. 5B illustrates a top view and a front view of a partially closed atraumatic forceps 510. In one or more embodiments, a compression of actuation structure 100 may be configured to gradually close an atraumatic forceps 400, e.g., from an open atraumatic forceps 500 to a partially closed atraumatic forceps 510. Illustratively, a compression of actuation structure 100 may be configured to extend actuation sleeve 260 relative to surgical blank 290, e.g., a compression of actuation structure 100 may be configured to extend actuation sleeve distal end 261 over atraumatic forceps jaws proximal ends 412. In one or more embodiments, a compression of actuation structure 100 may be configured to decrease a distance between a first atraumatic forceps jaw distal end 411 and a second atraumatic forceps jaw distal end 411, e.g., a first atraumatic forceps jaw distal end 411 and a second atraumatic forceps jaw distal end 411 may be separated by a distance less than distance 415 when atraumatic forceps 400 comprises a partially closed atraumatic forceps 510.

FIG. 5C illustrates a top view and a front view of a fully closed atraumatic forceps 520. Illustratively, a compression of actuation structure 100 may be configured to gradually close an atraumatic forceps 400, e.g., from a partially closed atraumatic forceps 510 to a fully closed atraumatic forceps 520. In one or more embodiments, a compression of actuation structure 100 may be configured to extend actuation sleeve 260 relative to surgical blank 290, e.g., a compression of actuation structure 100 may be configured to extend actuation sleeve distal end 261 over atraumatic forceps jaws proximal ends 412. Illustratively, an extension of actuation sleeve 260 over atraumatic forceps jaws proximal ends 412 may be configured to close atraumatic forceps jaws 410 wherein atraumatic forceps jaws 410 initially contact at atraumatic forceps jaws distal ends 411. In one or more embodiments, a compression of actuation structure 100 may be configured to gradually close atraumatic forceps jaws 410 wherein atraumatic forceps jaws 410 initially contact at atraumatic forceps jaws distal ends 411. Illustratively, after atraumatic forceps jaws distal ends 411 initially contact, a compression of actuation structure 100 may be configured to gradually close atraumatic forceps jaws 410 wherein a contact area between atraumatic forceps jaws 410 gradually increases. In one or more embodiments, atraumatic forceps jaws 410 may be configured to close wherein an amount of a first atraumatic forceps jaw 410 in contact with a second atraumatic forceps jaw 410 increases gradually from atraumatic forceps jaws distal ends 411, e.g., atraumatic forceps jaws 410 may be configured to close wherein an amount of a first atraumatic forceps jaw 410 in contact with a second atraumatic forceps jaw 410 increases gradually towards atraumatic forceps jaws proximal ends 412. Illustratively, a compression of actuation structure 100 may be configured to close atraumatic forceps jaws 410 starting at atraumatic forceps jaws distal ends 411 and gradually progressing towards atraumatic forceps jaws proximal ends 412. In one or more embodiments, a compression of actuation structure 100 may be configured to close a first atraumatic forceps jaw 410 and a second atraumatic forceps jaw 410 wherein the first and second atraumatic forceps jaws 410 initially contact each other at first and second atraumatic forceps jaws distal ends 411. Illustratively, after the first and second atraumatic forceps jaws 410 initially contact at first and second atraumatic forceps jaws distal ends 411, a compression of actuation structure 100 may be configured to cause medial portions of the first and second atraumatic forceps jaws 410 to gradually contact each other starting at medial portions of the first and second atraumatic forceps jaws 410 adjacent to first and second atraumatic forceps jaws distal ends 411.

In one or more embodiments, a surgeon may separate an internal limiting membrane from a retina by grasping the internal limiting membrane with atraumatic forceps jaws 410, e.g., without damaging the retina. Illustratively, a surgeon may manipulate actuation structure 100 and assembled surgical instrument 200 to approach a retina with atraumatic forceps 400, e.g., when atraumatic forceps 400 comprises an open atraumatic forceps 500. For example, a surgeon may gradually move atraumatic forceps jaws distal ends 411 closer to a retina until atraumatic forceps jaws distal ends 411 contact an internal limiting membrane. In one or more embodiments, a compression of actuation structure 100, e.g., by a surgeon, may be configured to extend actuation sleeve 260 over atraumatic forceps jaws proximal ends 412. Illustratively, a surgeon may grasp an internal limiting membrane with atraumatic forceps jaws distal ends 411 and no other portion of atraumatic forceps jaws 410, e.g., to minimize trauma to an underlying retinal tissue. For example, after a surgeon grasps a first portion of an internal limiting membrane with atraumatic forceps jaws distal ends 411, the surgeon may manipulate the first portion of the internal limiting membrane and compress actuation structure 100 to grasp a second portion of the internal limiting membrane with atraumatic forceps jaws 410. Illustratively, the surgeon may grasp the second portion of the internal limiting membrane with a portion of atraumatic forceps jaws 410 located a distance from atraumatic forceps jaws distal ends 411.

Figure 6A:
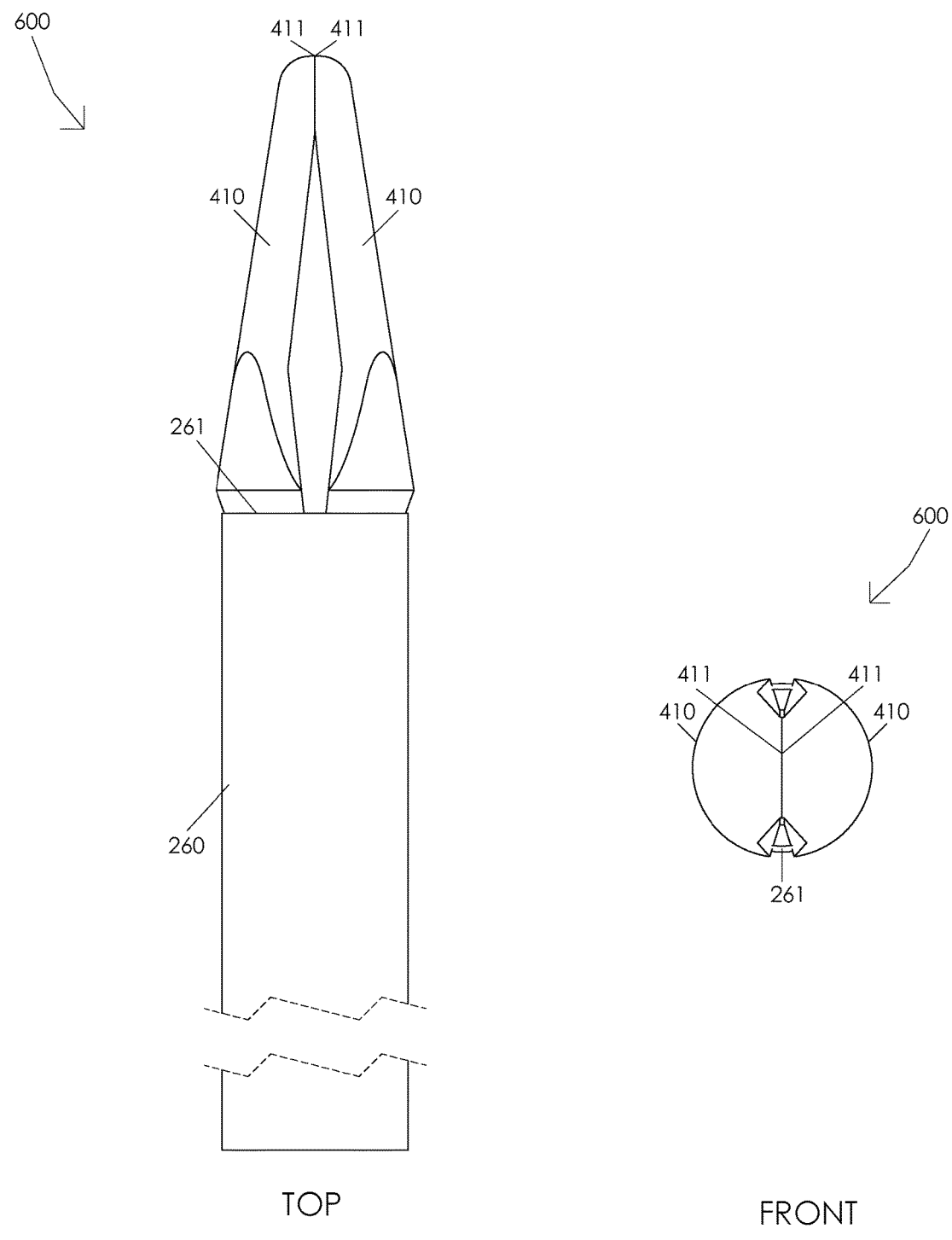
FIGS. 6A, 6B, and 6C are schematic diagrams illustrating a gradual opening of an atraumatic forceps.
Figure 6B:
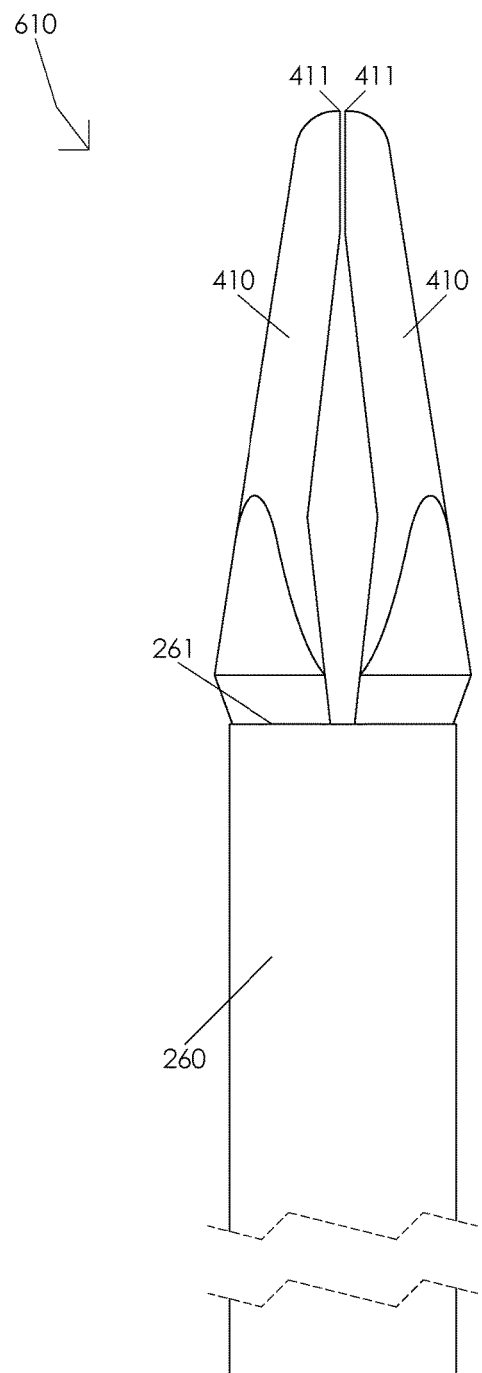
Figure 6B:
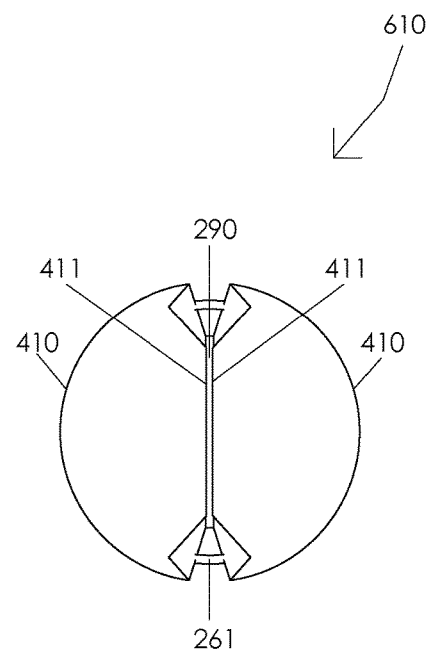
Figure 6C:
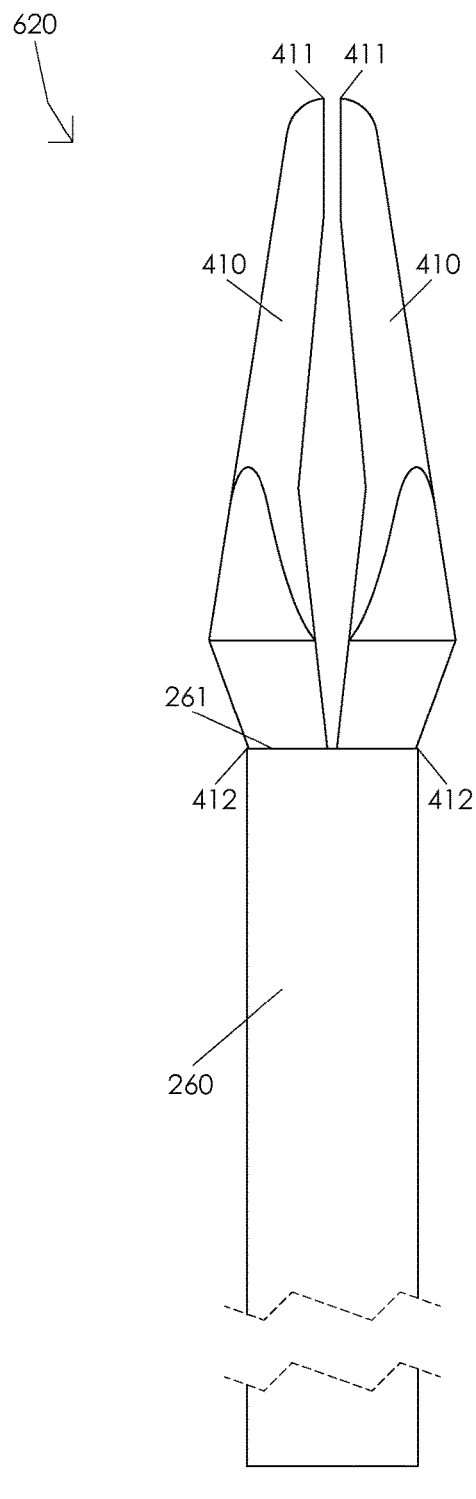
Figure 6C:
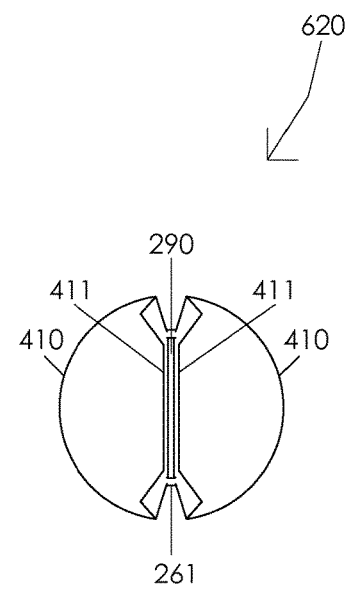

FIGS. 6A, 6B, and 6C are schematic diagrams illustrating a gradual opening of an atraumatic forceps 400. FIG. 6A illustrates a top view and a front view of a closed atraumatic forceps 600. In one or more embodiments, atraumatic forceps 400 may comprise a closed atraumatic forceps 600, e.g., when a first atraumatic forceps jaw distal end u) 411 is adjacent to a second atraumatic forceps jaw distal end 411. Illustratively, atraumatic forceps 400 may comprise a closed atraumatic forceps 600, e.g., when actuation sleeve 260 is fully extended over atraumatic forceps jaws proximal ends 412. Illustratively, atraumatic forceps 400 may comprise a closed atraumatic forceps 600, e.g., when actuation structure 100 is fully compressed.

FIG. 6B illustrates a top view and a front view of a partially open atraumatic forceps 610. In one or more embodiments, a decompression of actuation structure 100 may be configured to gradually open an atraumatic forceps 400, e.g., from a closed atraumatic forceps 600 to a partially open atraumatic forceps 610. Illustratively, a decompression of actuation structure 100 may be configured to retract actuation sleeve 260 relative to surgical blank 290, e.g., a decompression of actuation structure 100 may be configured to retract actuation sleeve distal end 261 relative to atraumatic forceps jaws proximal ends 412. In one or more embodiments, a decompression of actuation structure 100 may be configured to gradually separate atraumatic forceps jaws 410. Illustratively, a decompression of actuation structure 100 may be configured to gradually separate atraumatic forceps jaws 410 wherein a first atraumatic forceps jaw distal end 411 contacts a second atraumatic forceps jaw distal end 411 until all other portions of atraumatic forceps jaws 410 are separated. In one or more embodiments, a decompression of actuation structure 100 may be configured to separate atraumatic forceps jaws 410 wherein atraumatic forceps jaws distal ends 411 are the last portions of atraumatic forceps jaws 410 to separate.

FIG. 6C illustrates a top view and a front view of a fully open atraumatic forceps 620. Illustratively, a decompression of actuation structure 100 may be configured to gradually open an atraumatic forceps 400, e.g., from a partially open atraumatic forceps 610 to a fully open atraumatic forceps 620. In one or more embodiments, a decompression of actuation structure 100 may be configured to retract actuation sleeve 260 relative to surgical blank 290, e.g., a decompression of actuation structure 100 may be configured to retract actuation sleeve distal end 261 relative to atraumatic forceps jaws proximal ends 412. Illustratively, a decompression of actuation structure 100 may be configured to gradually separate atraumatic forceps jaws 410. In one or more embodiments, a first atraumatic forceps jaw distal end 411 and a second atraumatic forceps jaw distal end 411 may be separated by distance 415, e.g., when atraumatic forceps 400 comprises a fully open atraumatic forceps 620.

Figure 7:
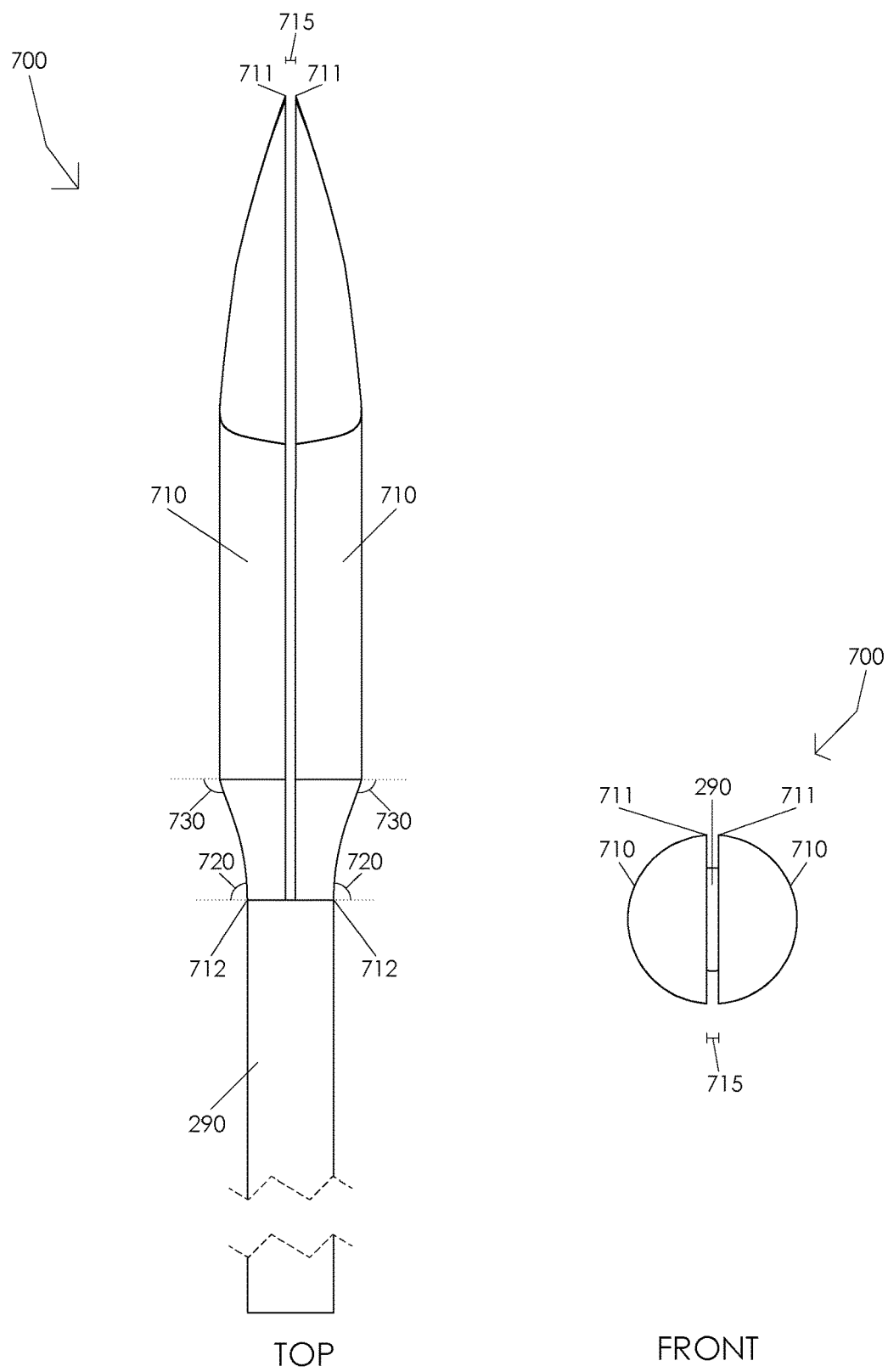
FIG. 7 is a schematic diagram illustrating an atraumatic forceps.

FIG. 7 is a schematic diagram illustrating an atraumatic forceps 700. FIG. 7 illustrates a top view and a front view of an atraumatic forceps 700. Illustratively, atraumatic forceps 700 may be manufactured with dimensions configured for performing microsurgical procedures, e.g., ophthalmic surgical procedures. In one or more embodiments, atraumatic forceps 700 may be manufactured from surgical blank 290. Illustratively, atraumatic forceps 700 may be manufactured by modifying surgical blank 290, e.g., with an electric discharge machine. In one or more embodiments, atraumatic forceps 700 may be manufactured by modifying surgical blank 290, e.g., with a laser, a file, or any suitable modification means. Illustratively, atraumatic forceps 700 may comprise a plurality of atraumatic forceps jaws 710, a fourth contour angle 720, and a fifth contour angle 730.

Illustratively, each atraumatic forceps jaw 710 of a plurality of atraumatic forceps jaws 710 may comprise an atraumatic forceps jaw distal end 711 and an atraumatic forceps jaw proximal end 712. In one or more embodiments, a first atraumatic forceps jaw distal end 711 and a second atraumatic forceps jaw distal end 711 may be separated by a distance 715. Illustratively, distance 715 may comprise a distance in a range of 0.005 to 0.08 inches, e.g., distance 715 may comprise a distance of 0.04 inches. In one or more embodiments, distance 715 may comprise a distance less than 0.005 inches or greater than 0.08 inches. Illustratively, atraumatic forceps 700 may be configured to separate a first tissue from a surface of a second tissue without damaging the second tissue. For example, atraumatic forceps 700 may be configured to separate a first tissue having a convex surface geometry from a second tissue having a convex surface geometry without damaging the second tissue. In one or more embodiments, the first tissue may comprise an internal limiting membrane and the second tissue may comprise a retina. Illustratively, distance 715 may comprise a distance in a range of 200 to 600 times an average thickness of the first tissue, e.g., distance 715 may comprise a distance 291 times the average thickness of the first tissue. In one or more embodiments, distance 715 may comprise a distance less than 200 times or greater than 600 times the average thickness of the first tissue. Illustratively, distance 715 may comprise a distance in a range of 200 to 600 times an average thickness of an internal limiting membrane, e.g., distance 715 may comprise a distance 291 times the average thickness of an internal limiting membrane. In one or more embodiments, distance 715 may comprise a distance less than 200 times or greater than 600 times the average thickness of an internal limiting membrane.

Illustratively, fourth contour angle 720 may comprise any angle less than 90 degrees, e.g., fourth contour angle 720 may comprise an angle in a range of 60 to 80 degrees. In one or more embodiments, fourth contour angle 720 may comprise an angle less than 60 degrees or greater than 80 degrees. Illustratively, fourth contour angle 720 may comprise a 76.3 degree angle. In one or more embodiments, fifth contour angle 730 may comprise any angle greater than 90 degrees, e.g., fifth contour angle 730 may comprise an angle in a range of 95 to 120 degrees. Illustratively, fifth contour angle 730 may comprise an angle less than 95 degrees or greater than 120 degrees. In one or more embodiments, fifth contour angle 730 may comprise a 103.7 degree angle.

In one or more embodiments, atraumatic forceps jaws 710 may be configured to close at atraumatic forceps jaws distal ends 711 as actuation sleeve 260 is gradually actuated over atraumatic forceps jaws proximal ends 712. Illustratively, an extension of actuation sleeve 260 relative to surgical blank 290 may be configured to decrease a distance 715 between a first atraumatic forceps jaw distal end 711 and a second atraumatic forceps jaw distal end 711. In one or more embodiments, an extension of actuation sleeve 260 over a first atraumatic forceps jaw proximal end 712 and a second atraumatic forceps jaw proximal end 712 may be configured to cause the first atraumatic forceps jaw distal end 711 and the second atraumatic forceps jaw distal end 711 to contact before any other portion of the first atraumatic forceps jaw 710 contacts any other portion of the second atraumatic forceps jaw 710.

Figure 8A:
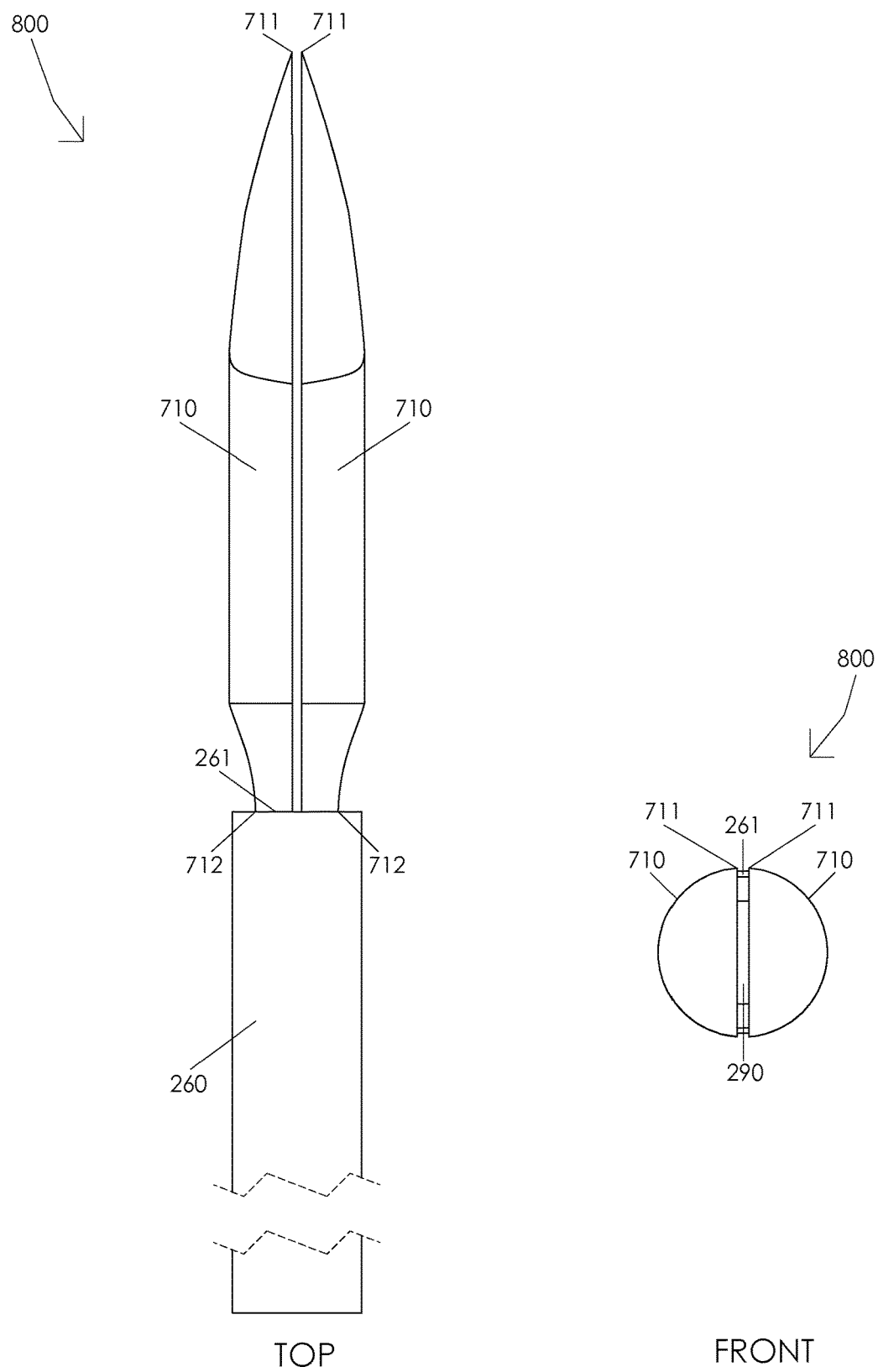
FIGS. 8A, 8B, and 8C are schematic diagrams illustrating a gradual closing of an atraumatic forceps.
Figure 8B:
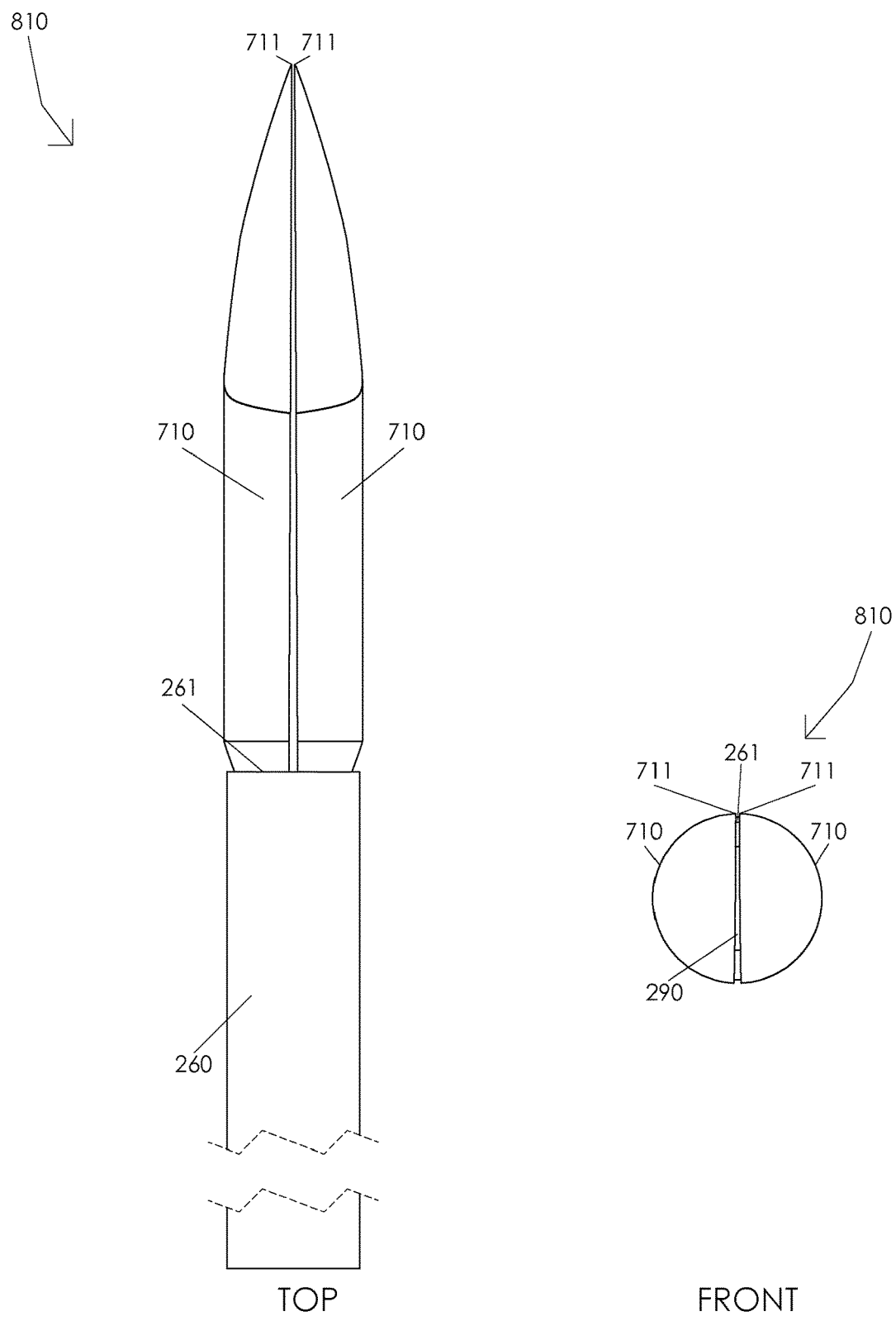
Figure 8C:
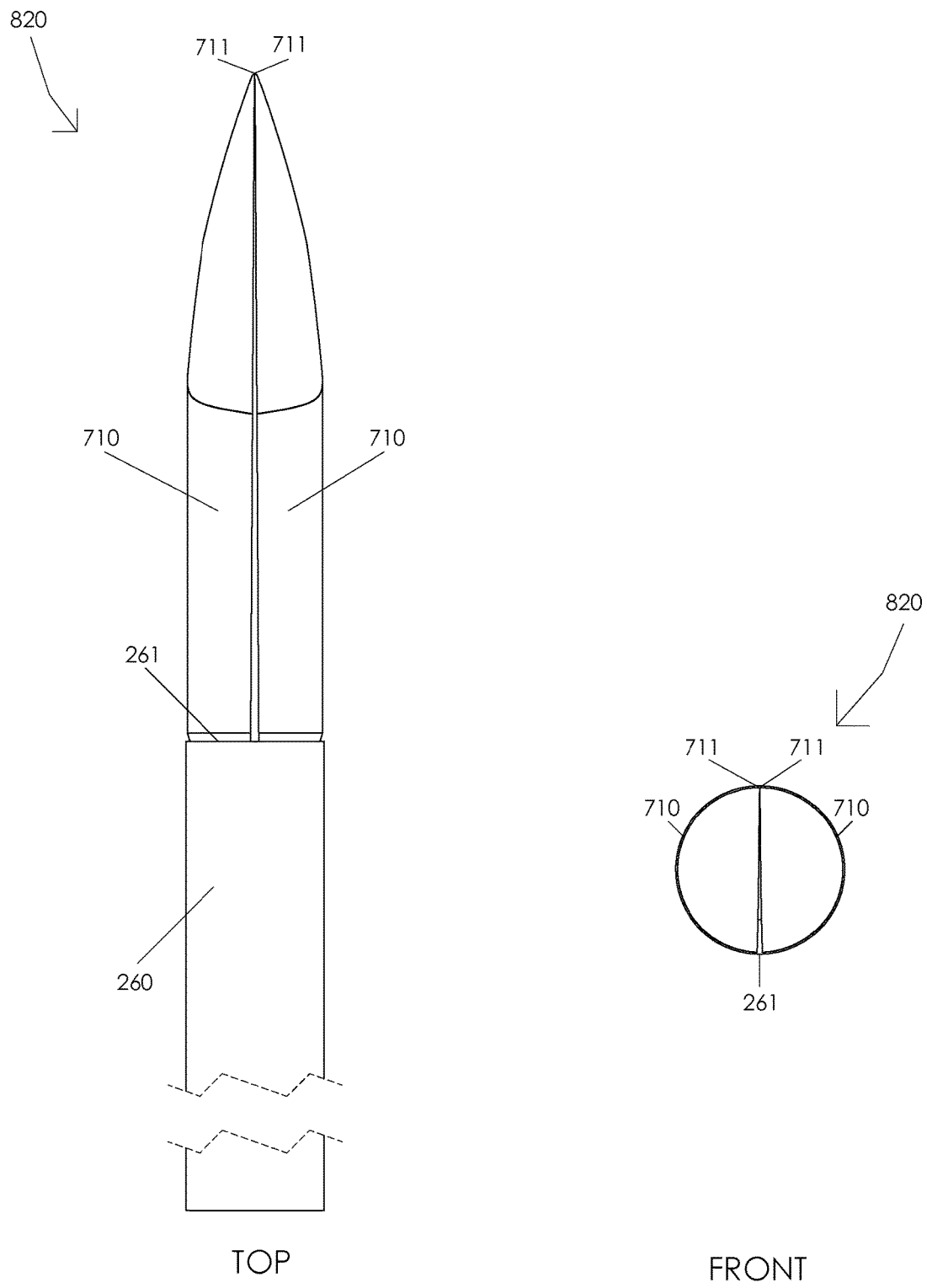

FIGS. 8A, 8B, and 8C are schematic diagrams illustrating a gradual closing of an atraumatic forceps 700. FIG. 8A illustrates a top view and a front view of an open atraumatic forceps 800. In one or more embodiments, atraumatic forceps 700 may comprise an open atraumatic forceps 800, e.g., when a first atraumatic forceps jaw distal end 711 is separated from a second atraumatic forceps jaw distal end 711 by distance 715. Illustratively, atraumatic forceps 700 may comprise an open atraumatic forceps 800, e.g., when actuation sleeve 260 is fully retracted relative to atraumatic forceps jaws proximal ends 712. Illustratively, atraumatic forceps 700 may comprise an open atraumatic forceps 800, e.g., when actuation structure 100 is fully decompressed.

FIG. 8B illustrates a top view and a front view of a partially closed atraumatic forceps 810. In one or more embodiments, a compression of actuation structure 100 may be configured to gradually close an atraumatic forceps 700, e.g., from an open atraumatic forceps 800 to a partially closed atraumatic forceps 810. Illustratively, a compression of actuation structure 100 may be configured to extend actuation sleeve 260 relative to surgical blank 290, e.g., a compression of actuation structure 100 may be configured to extend actuation sleeve distal end 261 over atraumatic forceps jaws proximal ends 712. In one or more embodiments, a compression of actuation structure 100 may be configured to decrease a distance between a first atraumatic forceps jaw distal end 711 and a second atraumatic forceps jaw distal end 711, e.g., a first atraumatic forceps jaw distal end 711 and a second atraumatic forceps jaw distal end 711 may be separated by a distance less than distance 715 when atraumatic forceps 700 comprises a partially closed atraumatic forceps 810.

FIG. 8C illustrates a top view and a front view of a fully closed atraumatic forceps 820. Illustratively, a compression of actuation structure 100 may be configured to gradually close an atraumatic forceps 700, e.g., from a partially closed atraumatic forceps 810 to a fully closed atraumatic forceps 820. In one or more embodiments, a compression of actuation structure 100 may be configured to extend actuation sleeve 260 relative to surgical blank 290, e.g., a compression of actuation structure 100 may be configured to extend actuation sleeve distal end 261 over atraumatic forceps jaws proximal ends 712. Illustratively, an extension of actuation sleeve 260 over atraumatic forceps jaws proximal ends 712 may be configured to close atraumatic forceps jaws 710 wherein atraumatic forceps jaws 710 initially contact at atraumatic forceps jaws distal ends 711. In one or more embodiments, a compression of actuation structure 100 may be configured to gradually close atraumatic forceps jaws 710 wherein atraumatic forceps jaws 710 initially contact at atraumatic forceps jaws distal ends 711. Illustratively, after atraumatic forceps jaws distal ends 711 initially contact, a compression of actuation structure 100 may be configured to gradually close atraumatic forceps jaws 710 wherein a contact area between atraumatic forceps jaws 710 gradually increases. In one or more embodiments, atraumatic forceps jaws 710 may be configured to close wherein an amount of a first atraumatic forceps jaw 710 in contact with a second atraumatic forceps jaw 710 increases gradually from atraumatic forceps jaws distal ends 711, e.g., atraumatic forceps jaws 710 may be configured to close wherein an amount of a first atraumatic forceps jaw 710 in contact with a second atraumatic forceps jaw 710 increases gradually towards atraumatic forceps jaws proximal ends 712. Illustratively, a compression of actuation structure 100 may be configured to close atraumatic forceps jaws 710 starting at atraumatic forceps jaws distal ends 711 and gradually progressing towards atraumatic forceps jaws proximal ends 712. In one or more embodiments, a compression of actuation structure 100 may be configured to close a first atraumatic forceps jaw 710 and a second atraumatic forceps jaw 710 wherein the first and second atraumatic forceps jaws 710 initially contact each other at first and second atraumatic forceps jaws distal ends 711. Illustratively, after the first and second atraumatic forceps jaws 710 initially contact at first and second atraumatic forceps jaws distal ends 711, a compression of actuation structure 100 may be configured to cause medial portions of the first and second atraumatic forceps jaws 710 to gradually contact each other starting at medial portions of the first and second atraumatic forceps jaws 710 adjacent to first and second atraumatic forceps jaws distal ends 711.

In one or more embodiments, a surgeon may separate an internal limiting membrane from a retina by grasping the internal limiting membrane with atraumatic forceps jaws 710, e.g., without damaging the retina. Illustratively, a surgeon may manipulate actuation structure 100 and assembled surgical instrument 200 to approach a retina with atraumatic forceps 700, e.g., when atraumatic forceps 700 comprises an open atraumatic forceps 800. For example, a surgeon may gradually move atraumatic forceps jaws distal ends 711 closer to a retina until atraumatic forceps jaws distal ends 711 contact an internal limiting membrane. In one or more embodiments, a compression of actuation structure 100, e.g., by a surgeon, may be configured to extend actuation sleeve 260 over atraumatic forceps jaws proximal ends 712. Illustratively, a surgeon may grasp an internal limiting membrane with atraumatic forceps jaws distal ends 711 and no other portion of atraumatic forceps jaws 710, e.g., to minimize trauma to an underlying retinal tissue. For example, after a surgeon grasps a first portion of an internal limiting membrane with atraumatic forceps jaws distal ends 711, the surgeon may manipulate the first portion of the internal limiting membrane and compress actuation structure 100 to grasp a second portion of the internal limiting membrane with atraumatic forceps jaws 710. Illustratively, the surgeon may grasp the second portion of the internal limiting membrane with a portion of atraumatic forceps jaws 710 located a distance from atraumatic forceps jaws distal ends 711.

Figure 9A:
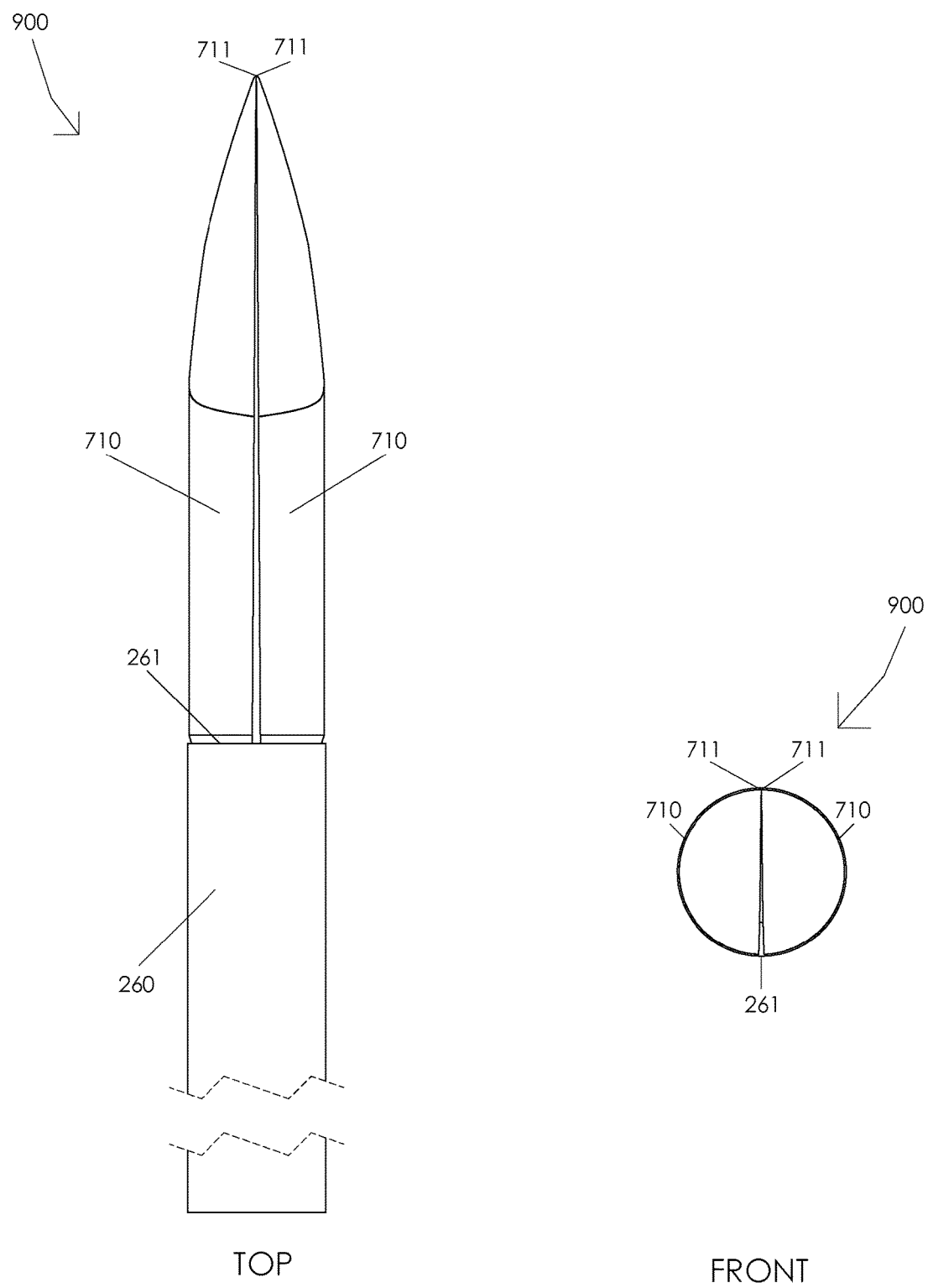
FIGS. 9A, 9B, and 9C are schematic diagrams illustrating a gradual opening of an atraumatic forceps.
Figure 9B:
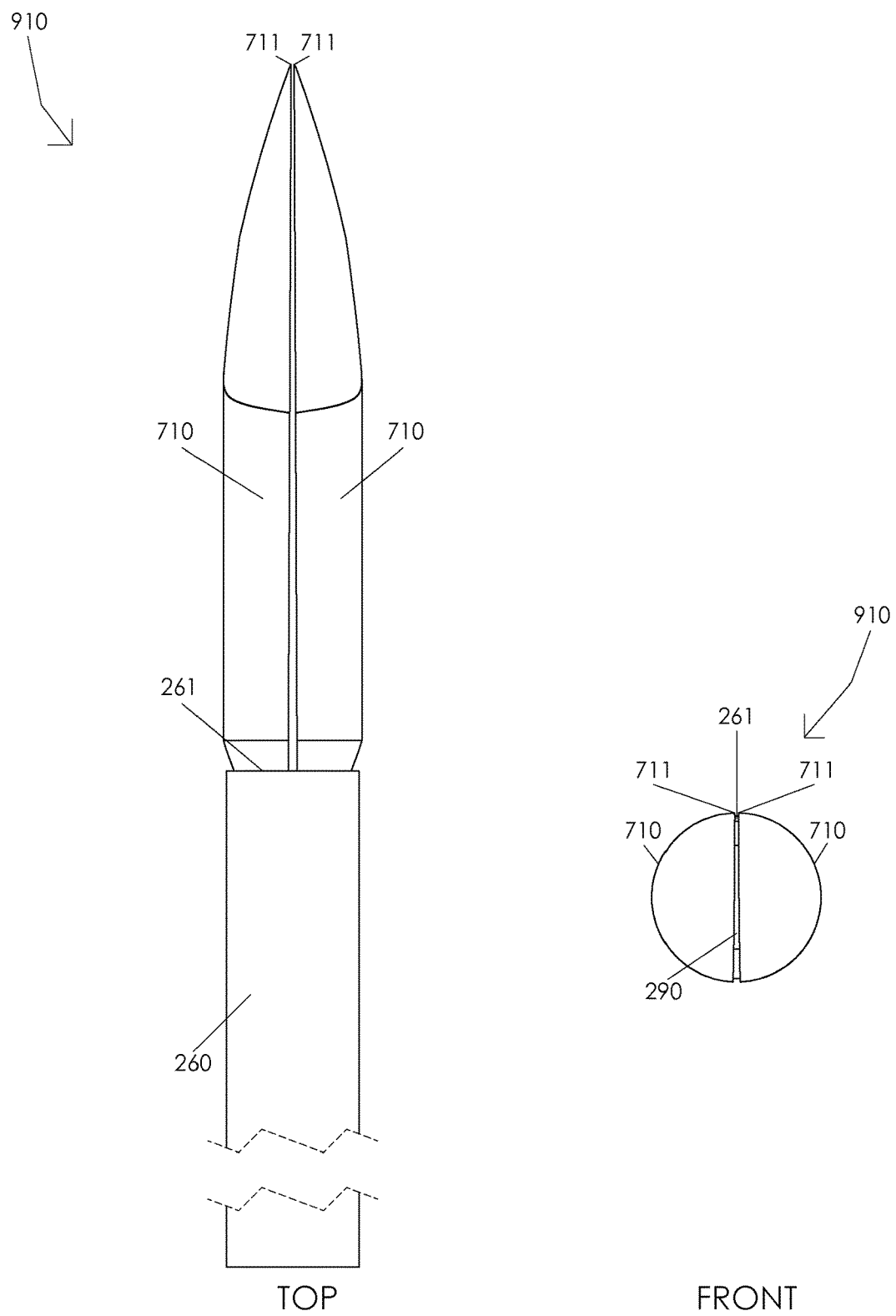
Figure 9C:
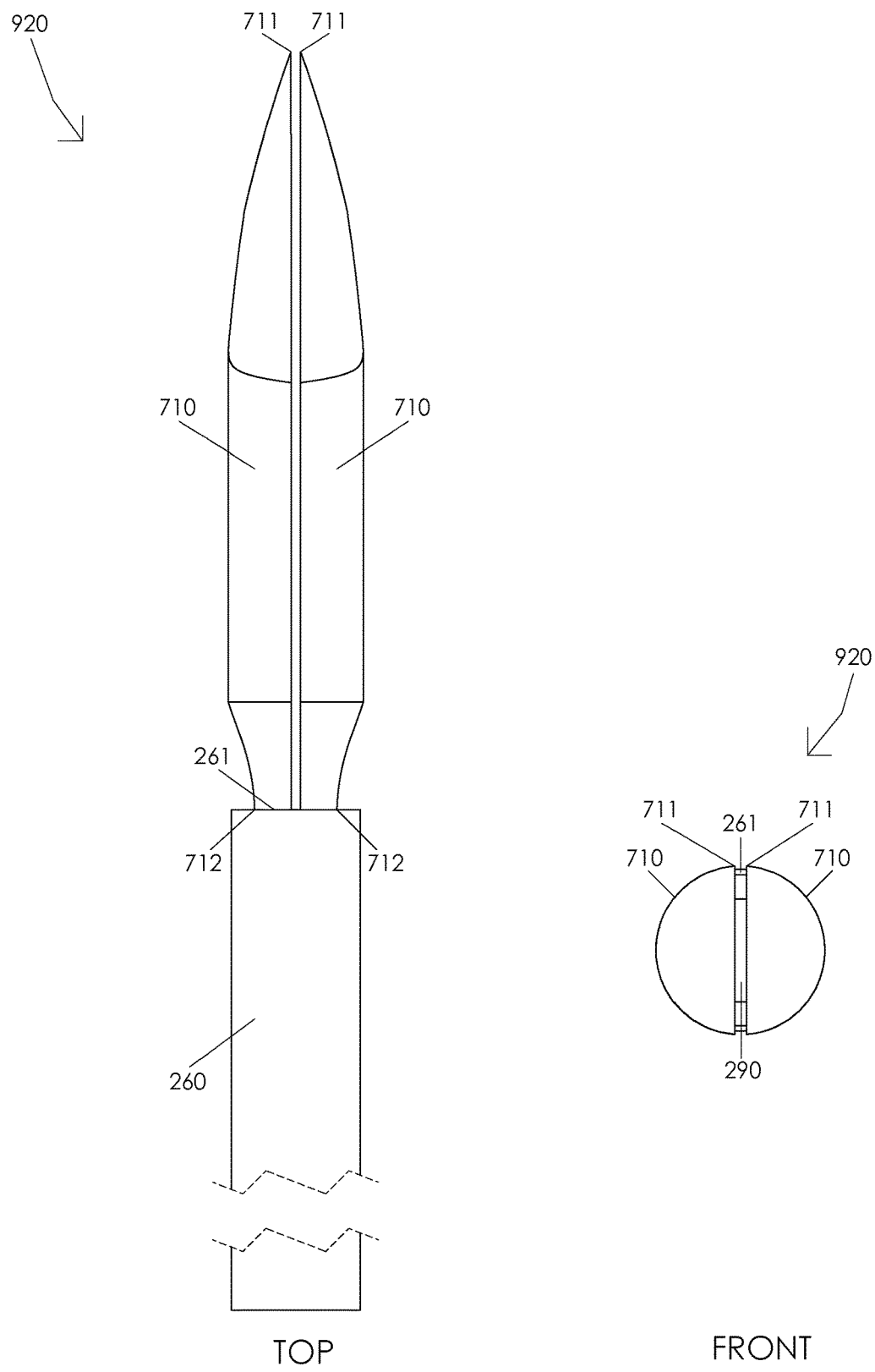

FIGS. 9A, 9B, and 9C are schematic diagrams illustrating a gradual opening of an atraumatic forceps 700. FIG. 9A illustrates a top view and a front view of a closed atraumatic forceps 900. In one or more embodiments, atraumatic forceps 700 may comprise a closed atraumatic forceps 900, e.g., when a first atraumatic forceps jaw distal end 711 is adjacent to a second atraumatic forceps jaw distal end 711. Illustratively, atraumatic forceps 700 may comprise a closed atraumatic forceps 900, e.g., when actuation sleeve 260 is fully extended over atraumatic forceps jaws proximal ends 712. Illustratively, atraumatic forceps 700 may comprise a closed atraumatic forceps 900, e.g., when actuation structure 100 is fully compressed.

FIG. 9B illustrates a top view and a front view of a partially open atraumatic forceps 910. In one or more embodiments, a decompression of actuation structure 100 may be configured to gradually open an atraumatic forceps 700, e.g., from a closed atraumatic forceps 900 to a partially open atraumatic forceps 910. Illustratively, a decompression of actuation structure 100 may be configured to retract actuation sleeve 260 relative to surgical blank 290, e.g., a decompression of actuation structure 100 may be configured to retract actuation sleeve distal end 261 relative to atraumatic forceps jaws proximal ends 712. In one or more embodiments, a decompression of actuation structure 100 may be configured to gradually separate atraumatic forceps jaws 710. Illustratively, a decompression of actuation structure 100 may be configured to gradually separate atraumatic forceps jaws 710 wherein a first atraumatic forceps jaw distal end 711 contacts a second atraumatic forceps jaw distal end 711 until all other portions of atraumatic forceps jaws 710 are separated. In one or more embodiments, a decompression of actuation structure 100 may be configured to separate atraumatic forceps jaws 710 wherein atraumatic forceps jaws distal ends 711 are the last portions of atraumatic forceps jaws 710 to separate.

FIG. 9C illustrates a top view and a front view of a fully open atraumatic forceps 920. Illustratively, a decompression of actuation structure 100 may be configured to gradually open an atraumatic forceps 700, e.g., from a partially open atraumatic forceps 910 to a fully open atraumatic forceps 920. In one or more embodiments, a decompression of actuation structure 100 may be configured to retract actuation sleeve 260 relative to surgical blank 290, e.g., a decompression of actuation structure 100 may be configured to retract actuation sleeve distal end 261 relative to atraumatic forceps jaws proximal ends 712. Illustratively, a decompression of actuation structure 100 may be configured to gradually separate atraumatic forceps jaws 710. In one or more embodiments, a first atraumatic forceps jaw distal end 711 and a second atraumatic forceps jaw distal end 711 may be separated by distance 715, e.g., when atraumatic forceps 700 comprises a fully open atraumatic forceps 920.

Figure 10:
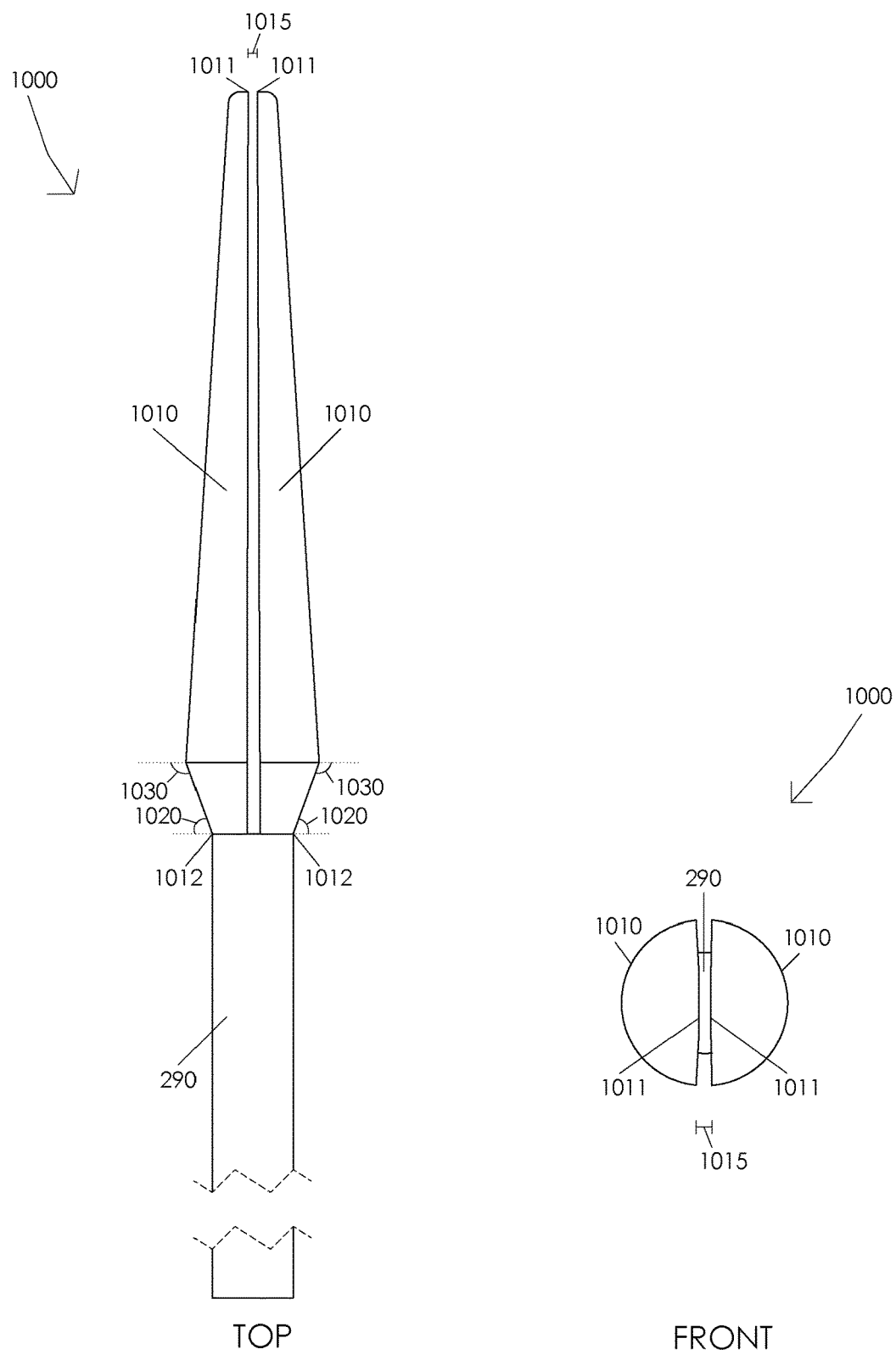
FIG. 10 is a schematic diagram illustrating an atraumatic forceps.

FIG. 10 is a schematic diagram illustrating an atraumatic forceps 1000. FIG. 10 illustrates a top view and a front view of an atraumatic forceps 1000. Illustratively, atraumatic forceps 1000 may be manufactured with dimensions configured for performing microsurgical procedures, e.g., ophthalmic surgical procedures. In one or more embodiments, atraumatic forceps 1000 may be manufactured from surgical blank 290. Illustratively, atraumatic forceps 1000 may be manufactured by modifying surgical blank 290, e.g., with an electric discharge machine. In one or more embodiments, atraumatic forceps 1000 may be manufactured by modifying surgical blank 290, e.g., with a laser, a file, or any suitable modification means. Illustratively, atraumatic forceps 1000 may comprise a plurality of atraumatic forceps jaws 1010, a sixth contour angle 1020, and a seventh contour angle 1030.

Illustratively, each atraumatic forceps jaw 1010 of a plurality of atraumatic forceps jaws 1010 may comprise an atraumatic forceps jaw distal end 1011 and an atraumatic forceps jaw proximal end 1012. In one or more embodiments, a first atraumatic forceps jaw distal end 1011 and a second atraumatic forceps jaw distal end 1011 may be separated by a distance 1015. Illustratively, distance 1015 may comprise a distance in a range of 0.005 to 0.08 inches, e.g., distance 1015 may comprise a distance of 0.04 inches. In one or more embodiments, distance 1015 may comprise a distance less than 0.005 inches or greater than 0.08 inches. Illustratively, atraumatic forceps 1000 may be configured to separate a first tissue from a surface of a second tissue without damaging the second tissue. For example, atraumatic forceps 1000 may be configured to separate a first tissue having a convex surface geometry from a second tissue having a convex surface geometry without damaging the second tissue. In one or more embodiments, the first tissue may comprise an internal limiting membrane and the second tissue may comprise a retina. Illustratively, distance 1015 may comprise a distance in a range of 200 to 600 times an average thickness of the first tissue, e.g., distance 1015 may comprise a distance 291 times the average thickness of the first tissue. In one or more embodiments, distance 1015 may comprise a distance less than 200 times or greater than 600 times the average thickness of the first tissue. Illustratively, distance 1015 may comprise a distance in a range of 200 to 600 times an average thickness of an internal limiting membrane, e.g., distance 1015 may comprise a distance 291 times the average thickness of an internal limiting membrane. In one or more embodiments, distance 1015 may comprise a distance less than 200 times or greater than 600 times the average thickness of an internal limiting membrane.

Illustratively, sixth contour angle 1020 may comprise any angle less than 90 degrees, e.g., sixth contour angle 1020 may comprise an angle in a range of 60 to 80 degrees. In one or more embodiments, sixth contour angle 1020 may comprise an angle less than 60 degrees or greater than 80 degrees. Illustratively, sixth contour angle 1020 may comprise a 70 degree angle. In one or more embodiments, seventh contour angle 1030 may comprise any angle greater than 90 degrees, e.g., seventh contour angle 1030 may comprise an angle in a range of 95 to 120 degrees. Illustratively, seventh contour angle 1030 may comprise an angle less than 95 degrees or greater than 120 degrees. In one or more embodiments, seventh contour angle 1030 may comprise a 110 degree angle.

In one or more embodiments, atraumatic forceps jaws 1010 may be configured to close at atraumatic forceps jaws distal ends 1011 as actuation sleeve 260 is gradually actuated over atraumatic forceps jaws proximal ends 1012. Illustratively, an extension of actuation sleeve 260 relative to surgical blank 290 may be configured to decrease a distance 1015 between a first atraumatic forceps jaw distal end 1011 and a second atraumatic forceps jaw distal end 1011. In one or more embodiments, an extension of actuation sleeve 260 over a first atraumatic forceps jaw proximal end 1012 and a second atraumatic forceps jaw proximal end 1012 may be configured to cause the first atraumatic forceps jaw distal end 1011 and the second atraumatic forceps jaw distal end 1011 to contact before any other portion of the first atraumatic forceps jaw 1010 contacts any other portion of the second atraumatic forceps jaw 1010.

Figure 11A:
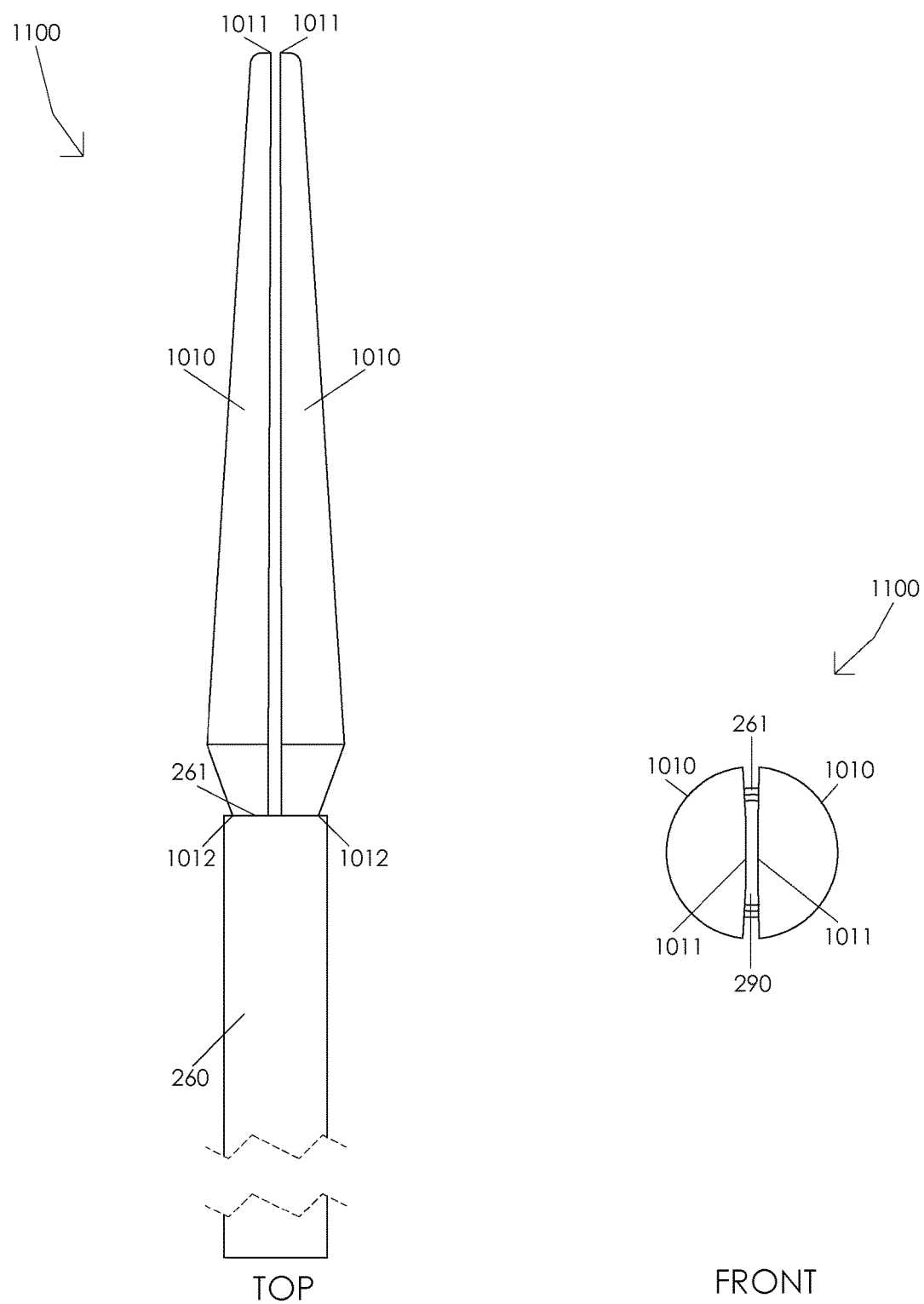
FIGS. 11A, 11B, and 11C are schematic diagrams illustrating a gradual closing of an atraumatic forceps.
Figure 11B:
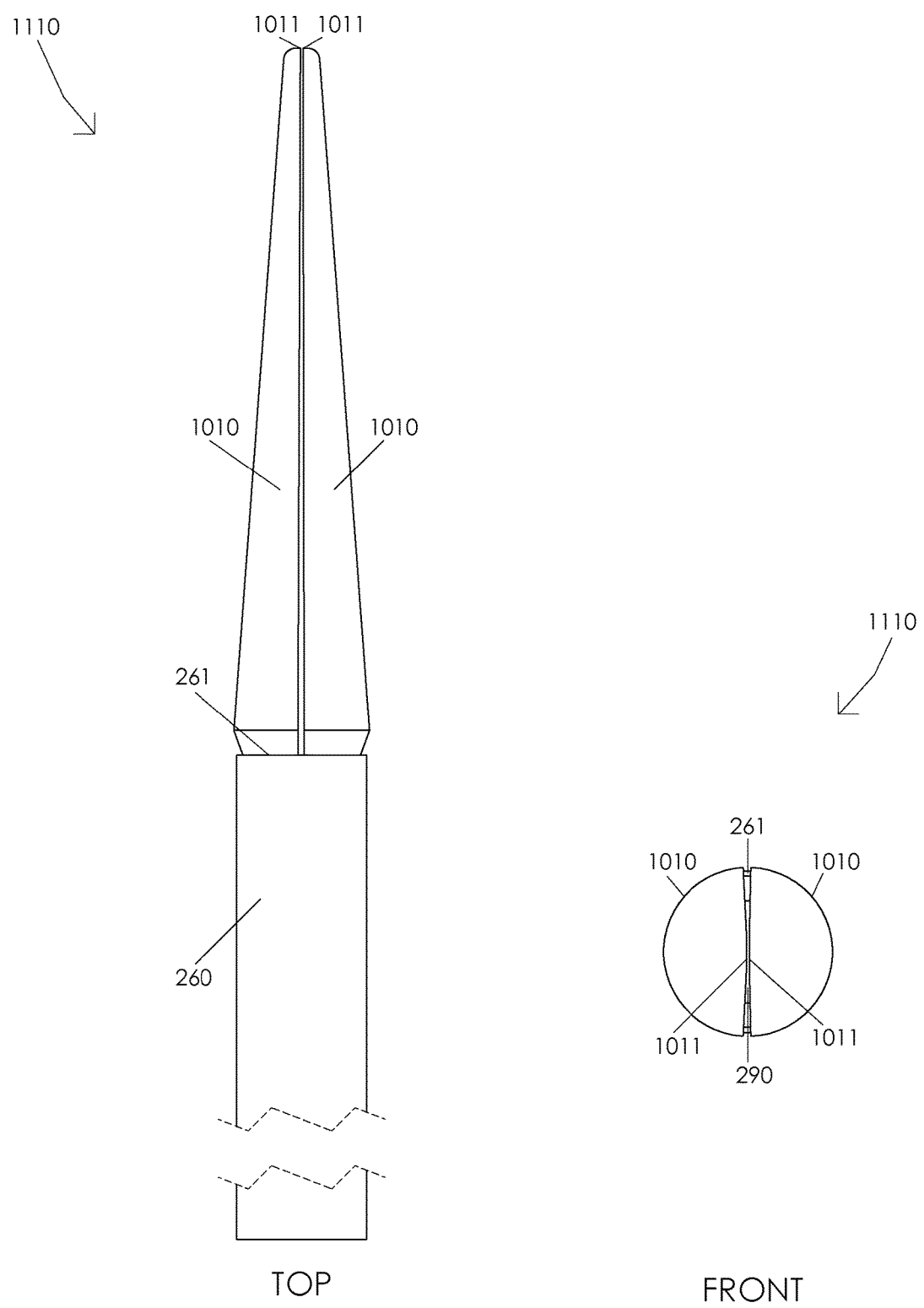
Figure 11C:
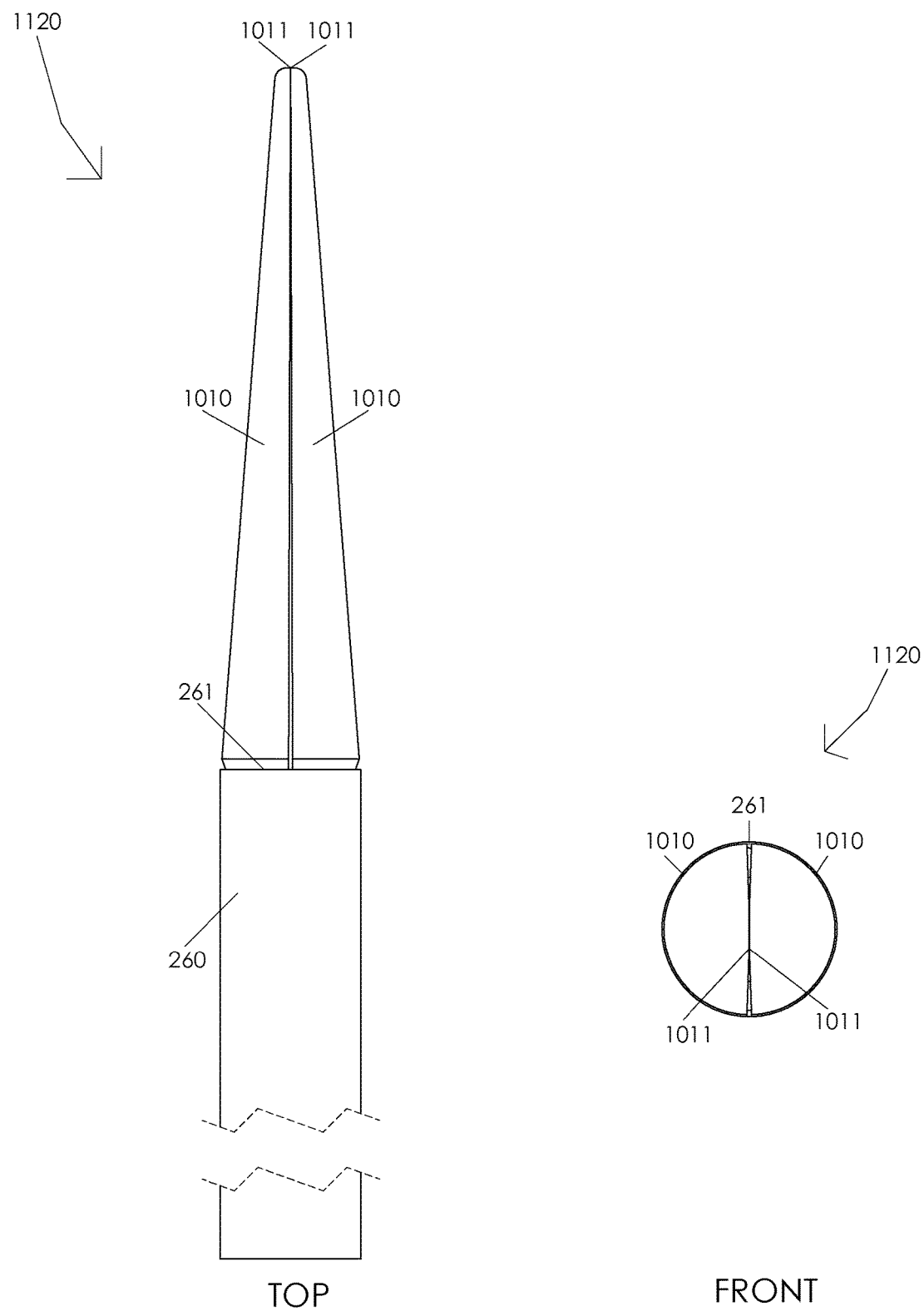

FIGS. 11A, 11B, and 11C are schematic diagrams illustrating a gradual closing of an atraumatic forceps 1000. FIG. 11A illustrates a top view and a front view of an open atraumatic forceps 1100. In one or more embodiments, atraumatic forceps 1000 may comprise an open atraumatic forceps 1100, e.g., when a first atraumatic forceps jaw distal end 1011 is separated from a second atraumatic forceps jaw distal end 1011 by distance 1015. Illustratively, atraumatic forceps 1000 may comprise an open atraumatic forceps 1100, e.g., when actuation sleeve 260 is fully retracted relative to atraumatic forceps jaws proximal ends 1012. Illustratively, atraumatic forceps 1000 may comprise an open atraumatic forceps 1100, e.g., when actuation structure 100 is fully decompressed.

FIG. 11B illustrates a top view and a front view of a partially closed atraumatic forceps 1110. In one or more embodiments, a compression of actuation structure 100 may be configured to gradually close an atraumatic forceps 1000, e.g., from an open atraumatic forceps 1100 to a partially closed atraumatic forceps 1110. Illustratively, a compression of actuation structure 100 may be configured to extend actuation sleeve 260 relative to surgical blank 290, e.g., a compression of actuation structure 100 may be configured to extend actuation sleeve distal end 261 over atraumatic forceps jaws proximal ends 1012. In one or more embodiments, a compression of actuation structure 100 may be configured to decrease a distance between a first atraumatic forceps jaw distal end 1011 and a second atraumatic forceps jaw distal end 1011, e.g., a first atraumatic forceps jaw distal end 1011 and a second atraumatic forceps jaw distal end 1011 may be separated by a distance less than distance 1015 when atraumatic forceps 1000 comprises a partially closed atraumatic forceps 1110.

FIG. 11C illustrates a top view and a front view of a fully closed atraumatic forceps 1120. Illustratively, a compression of actuation structure 100 may be configured to gradually close an atraumatic forceps 1000, e.g., from a partially closed atraumatic forceps 1110 to a fully closed atraumatic forceps 1120. In one or more embodiments, a compression of actuation structure 100 may be configured to extend actuation sleeve 260 relative to surgical blank 290, e.g., a compression of actuation structure 100 may be configured to extend actuation sleeve distal end 261 over atraumatic forceps jaws proximal ends 1012. Illustratively, an extension of actuation sleeve 260 over atraumatic forceps jaws proximal ends 1012 may be configured to close atraumatic forceps jaws 1010 wherein atraumatic forceps jaws 1010 initially contact at atraumatic forceps jaws distal ends 1011. In one or more embodiments, a compression of actuation structure 100 may be configured to gradually close atraumatic forceps jaws 1010 wherein atraumatic forceps jaws 1010 initially contact at atraumatic forceps jaws distal ends 1011. Illustratively, after atraumatic forceps jaws distal ends 1011 initially contact, a compression of actuation structure 100 may be configured to gradually close atraumatic forceps jaws 1010 wherein a contact area between atraumatic forceps jaws 1010 gradually increases. In one or more embodiments, atraumatic forceps jaws 1010 may be configured to close wherein an amount of a first atraumatic forceps jaw 1010 in contact with a second atraumatic forceps jaw 1010 increases gradually from atraumatic forceps jaws distal ends 1011, e.g., atraumatic forceps jaws 1010 may be configured to close wherein an amount of a first atraumatic forceps jaw 1010 in contact with a second atraumatic forceps jaw 1010 increases gradually towards atraumatic forceps jaws proximal ends 1012. Illustratively, a compression of actuation structure 100 may be configured to close atraumatic forceps jaws 1010 starting at atraumatic forceps jaws distal ends 1011 and gradually progressing towards atraumatic forceps jaws proximal ends 1012. In one or more embodiments, a compression of actuation structure 100 may be configured to close a first atraumatic forceps jaw 1010 and a second atraumatic forceps jaw 1010 wherein the first and second atraumatic forceps jaws 1010 initially contact each other at first and second atraumatic forceps jaws distal ends 1011. Illustratively, after the first and second atraumatic forceps jaws 1010 initially contact at first and second atraumatic forceps jaws distal ends 1011, a compression of actuation structure 100 may be configured to cause medial portions of the first and second atraumatic forceps jaws 1010 to gradually contact each other starting at medial portions of the first and second atraumatic forceps jaws 1010 adjacent to first and second atraumatic forceps jaws distal ends 1011.

In one or more embodiments, a surgeon may separate an internal limiting membrane from a retina by grasping the internal limiting membrane with atraumatic forceps jaws 1010, e.g., without damaging the retina. Illustratively, a surgeon may manipulate actuation structure 100 and assembled surgical instrument 200 to approach a retina with atraumatic forceps 1000, e.g., when atraumatic forceps 1000 comprises an open atraumatic forceps 1100. For example, a surgeon may gradually move atraumatic forceps jaws distal ends 1011 closer to a retina until atraumatic forceps jaws distal ends 1011 contact an internal limiting membrane. In one or more embodiments, a compression of actuation structure 100, e.g., by a surgeon, may be configured to extend actuation sleeve 260 over atraumatic forceps jaws proximal ends 1012. Illustratively, a surgeon may grasp an internal limiting membrane with atraumatic forceps jaws distal ends 1011 and no other portion of atraumatic forceps jaws 1010, e.g., to minimize trauma to an underlying retinal tissue. For example, after a surgeon grasps a first portion of an internal limiting membrane with atraumatic forceps jaws distal ends 1011, the surgeon may manipulate the first portion of the internal limiting membrane and compress actuation structure 100 to grasp a second portion of the internal limiting membrane with atraumatic forceps jaws 1010. Illustratively, the surgeon may grasp the second portion of the internal limiting membrane with a portion of atraumatic forceps jaws 1010 located a distance from atraumatic forceps jaws distal ends 1011.

Figure 12A:
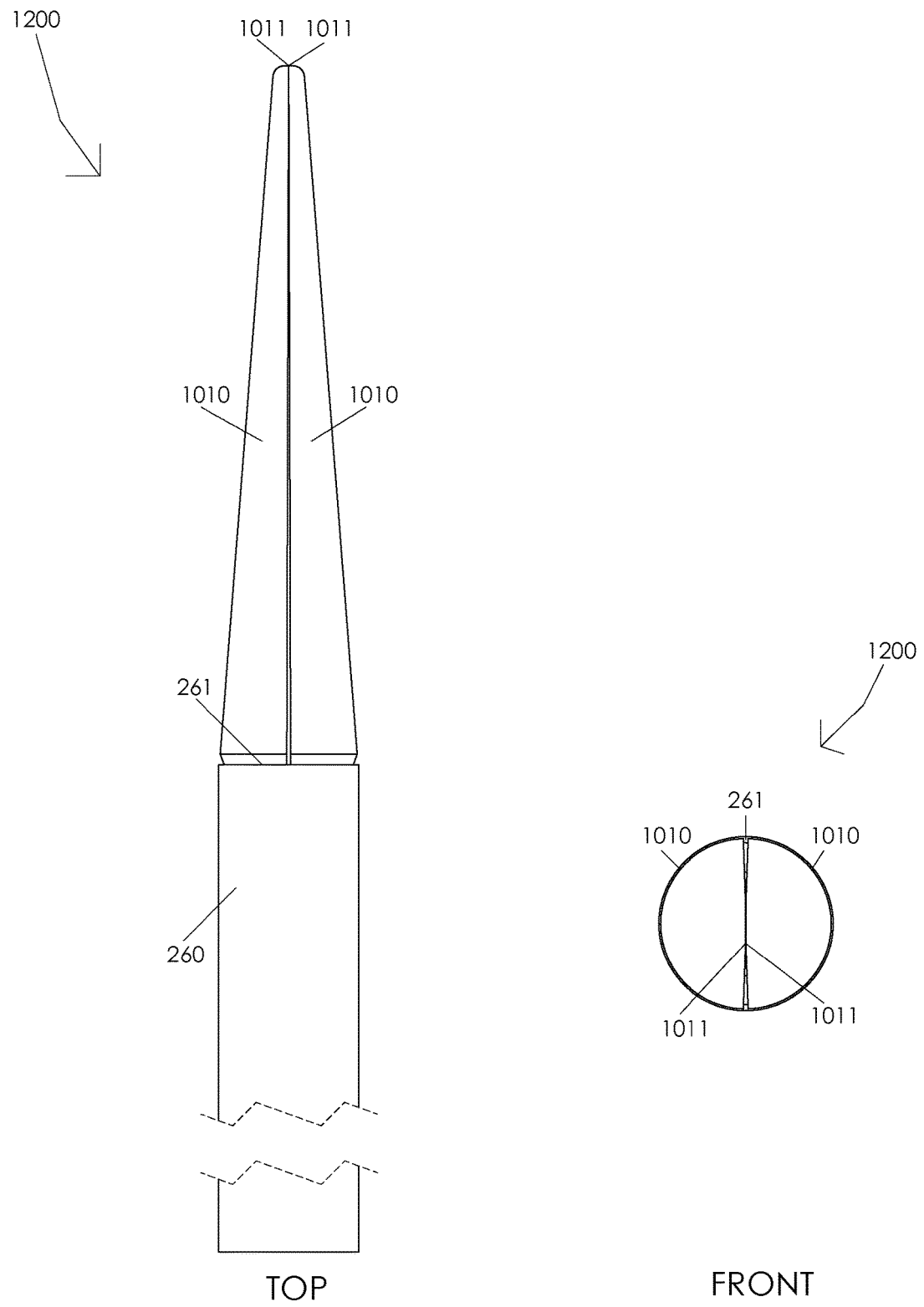
FIGS. 12A, 12B, and 12C are schematic diagrams illustrating a gradual opening of an atraumatic forceps.
Figure 12B:
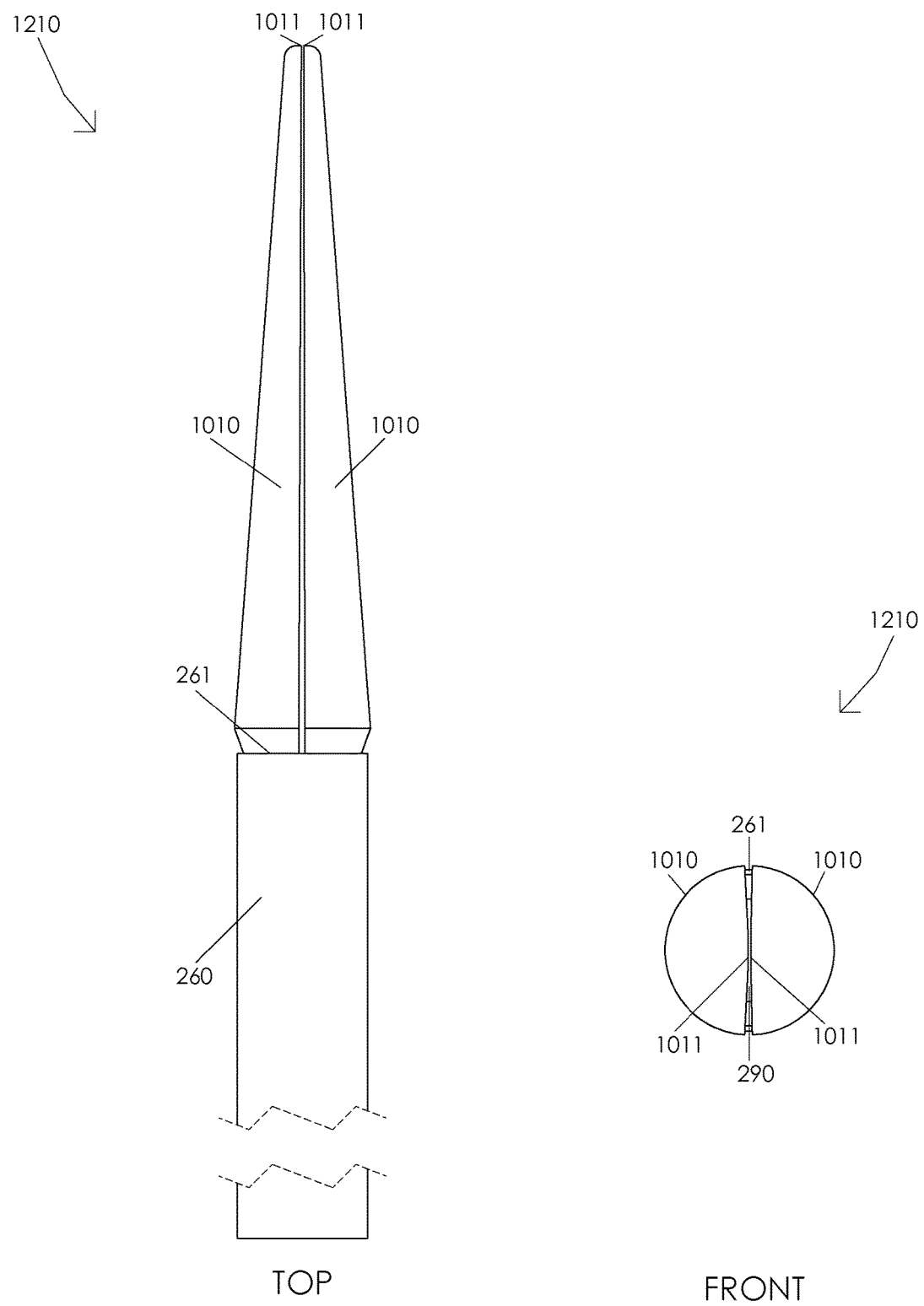
Figure 12C:
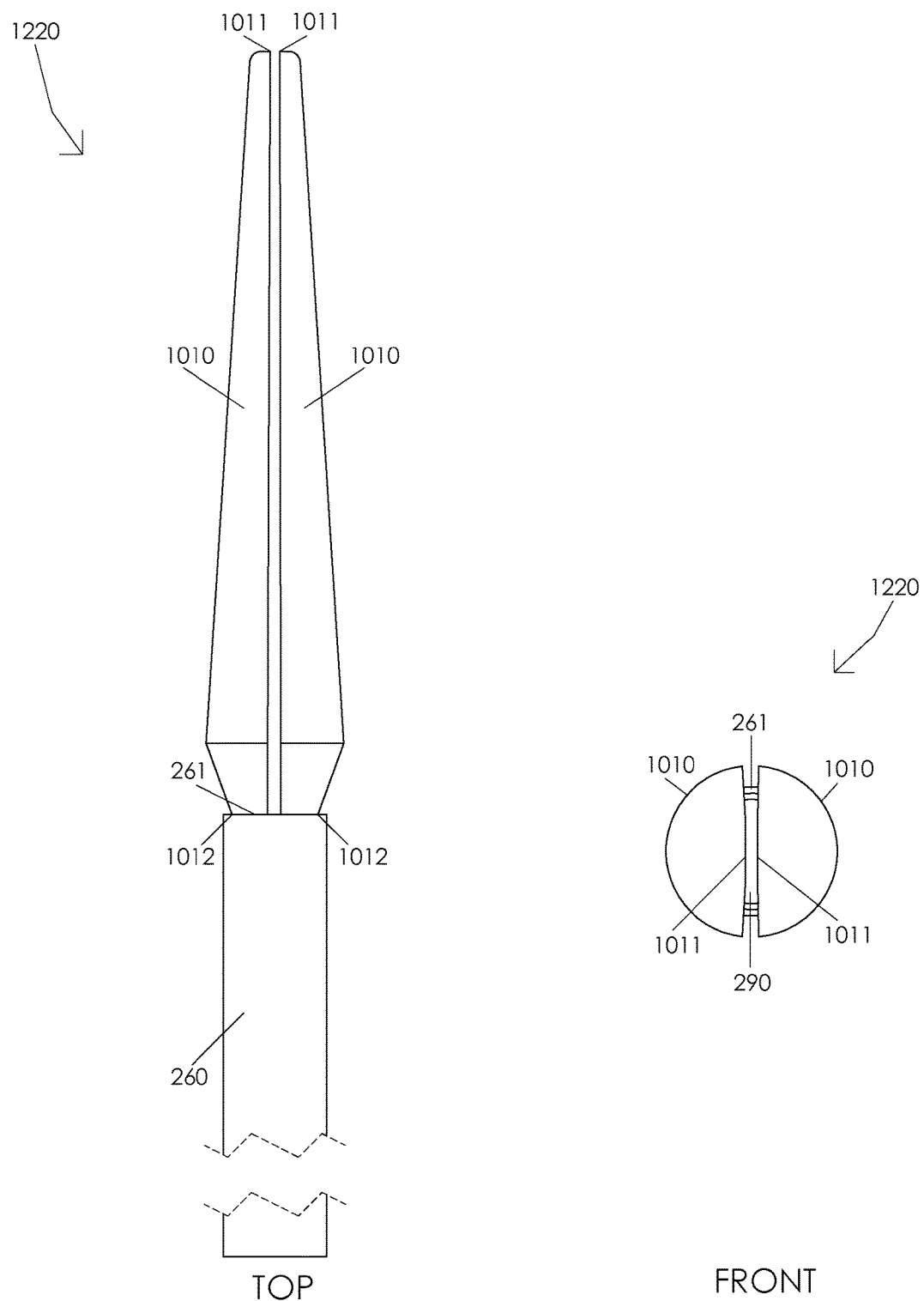

FIGS. 12A, 12B, and 12C are schematic diagrams illustrating a gradual opening of an atraumatic forceps 1000. FIG. 12A illustrates a top view and a front view of a closed atraumatic forceps 1200. In one or more embodiments, atraumatic forceps 1000 may comprise a closed atraumatic forceps 1200, e.g., when a first atraumatic forceps jaw distal end 1011 is adjacent to a second atraumatic forceps jaw distal end 1011. Illustratively, atraumatic forceps 1000 may comprise a closed atraumatic forceps 1200, e.g., when actuation sleeve 260 is fully extended over atraumatic forceps jaws proximal ends 1012. Illustratively, atraumatic forceps 1000 may comprise a closed atraumatic forceps 1200, e.g., when actuation structure 100 is fully compressed.

FIG. 12B illustrates a top view and a front view of a partially open atraumatic forceps 1210. In one or more embodiments, a decompression of actuation structure 100 may be configured to gradually open an atraumatic forceps 1000, e.g., from a closed atraumatic forceps 1200 to a partially open atraumatic forceps 1210. Illustratively, a decompression of actuation structure 100 may be configured to retract actuation sleeve 260 relative to surgical blank 290, e.g., a decompression of actuation structure 100 may be configured to retract actuation sleeve distal end 261 relative to atraumatic forceps jaws proximal ends 1012. In one or more embodiments, a decompression of actuation structure 100 may be configured to gradually separate atraumatic forceps jaws 1010. Illustratively, a decompression of actuation structure 100 may be configured to gradually separate atraumatic forceps jaws 1010 wherein a first atraumatic forceps jaw distal end 1011 contacts a second atraumatic forceps jaw distal end 1011 until all other portions of atraumatic forceps jaws 1010 are separated. In one or more embodiments, a decompression of actuation structure 100 may be configured to separate atraumatic forceps jaws 1010 wherein atraumatic forceps jaws distal ends 1011 are the last portions of atraumatic forceps jaws 1010 to separate.

FIG. 12C illustrates a top view and a front view of a fully open atraumatic forceps 1220. Illustratively, a decompression of actuation structure 100 may be configured to gradually open an atraumatic forceps 1000, e.g., from a partially open atraumatic forceps 1210 to a fully open atraumatic forceps 1220. In one or more embodiments, a decompression of actuation structure 100 may be configured to retract actuation sleeve 260 relative to surgical blank 290, e.g., a decompression of actuation structure 100 may be configured to retract actuation sleeve distal end 261 relative to atraumatic forceps jaws proximal ends 1012. Illustratively, a decompression of actuation structure 100 may be configured to gradually separate atraumatic forceps jaws 1010. In one or more embodiments, a first atraumatic forceps jaw distal end 1011 and a second atraumatic forceps jaw distal end 1011 may be separated by distance 1015, e.g., when atraumatic forceps 1000 comprises a fully open atraumatic forceps 1220.

Figure 13:
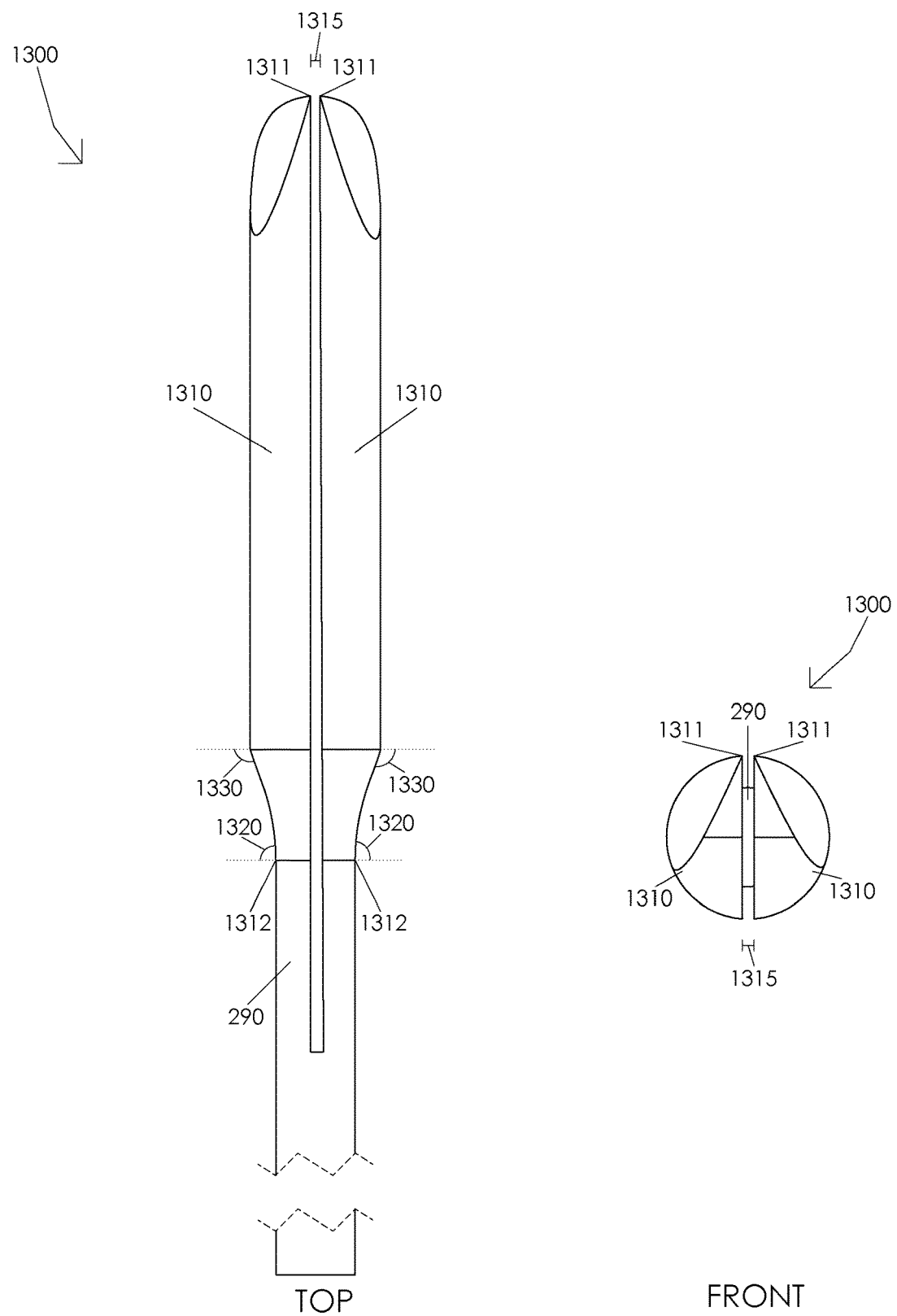
FIG. 13 is a schematic diagram illustrating an atraumatic forceps.

FIG. 13 is a schematic diagram illustrating an atraumatic forceps 1300. FIG. 13 illustrates a top view and a front view of an atraumatic forceps 1300. Illustratively, atraumatic forceps 1300 may be manufactured with dimensions configured for performing microsurgical procedures, e.g., ophthalmic surgical procedures. In one or more embodiments, atraumatic forceps 1300 may be manufactured from surgical blank 290. Illustratively, atraumatic forceps 1300 may be manufactured by modifying surgical blank 290, e.g., with an electric discharge machine. In one or more embodiments, atraumatic forceps 1300 may be manufactured by modifying surgical blank 290, e.g., with a laser, a file, or any suitable modification means. Illustratively, atraumatic forceps 1300 may comprise a plurality of atraumatic forceps jaws 1310, an eighth contour angle 1320, and a ninth contour angle 1330.

Illustratively, each atraumatic forceps jaw 1310 of a plurality of atraumatic forceps jaws 1310 may comprise an atraumatic forceps jaw distal end 1311 and an atraumatic forceps jaw proximal end 1312. In one or more embodiments, a first atraumatic forceps jaw distal end 1311 and a second atraumatic forceps jaw distal end 1311 may be separated by a distance 1315. Illustratively, distance 1315 may comprise a distance in a range of 0.005 to 0.08 inches, e.g., distance 1315 may comprise a distance of 0.04 inches. In one or more embodiments, distance 1315 may comprise a distance less than 0.005 inches or greater than 0.08 inches. Illustratively, atraumatic forceps 1300 may be configured to separate a first tissue from a surface of a second tissue without damaging the second tissue. For example, atraumatic forceps 1300 may be configured to separate a first tissue having a convex surface geometry from a second tissue having a convex surface geometry without damaging the second tissue. In one or more embodiments, the first tissue may comprise an internal limiting membrane and the second tissue may comprise a retina. Illustratively, distance 1315 may comprise a distance in a range of 200 to 600 times an average thickness of the first tissue, e.g., distance 1315 may comprise a distance 291 times the average thickness of the first tissue. In one or more embodiments, distance 1315 may comprise a distance less than 200 times or greater than 600 times the average thickness of the first tissue. Illustratively, distance 1315 may comprise a distance in a range of 200 to 600 times an average thickness of an internal limiting membrane, e.g., distance 1315 may comprise a distance 291 times the average thickness of an internal limiting membrane. In one or more embodiments, distance 1315 may comprise a distance less than 200 times or greater than 600 times the average thickness of an internal limiting membrane.

Illustratively, eighth contour angle 1320 may comprise any angle less than 90 degrees, e.g., eighth contour angle 1320 may comprise an angle in a range of 60 to 80 degrees. In one or more embodiments, eighth contour angle 1320 may comprise an angle less than 60 degrees or greater than 80 degrees. Illustratively, eighth contour angle 1320 may comprise a 72.3 degree angle. In one or more embodiments, ninth contour angle 1330 may comprise any angle greater than 90 degrees, e.g., ninth contour angle 1330 may comprise an angle in a range of 95 to 120 degrees. Illustratively, ninth contour angle 1330 may comprise an angle less than 95 degrees or greater than 120 degrees. In one or more embodiments, ninth contour angle 1330 may comprise a 107 degree angle.

In one or more embodiments, atraumatic forceps jaws 1310 may be configured to close at atraumatic forceps jaws distal ends 1311 as actuation sleeve 260 is gradually actuated over atraumatic forceps jaws proximal ends 1312. Illustratively, an extension of actuation sleeve 260 relative to surgical blank 290 may be configured to decrease a distance 1315 between a first atraumatic forceps jaw distal end 1311 and a second atraumatic forceps jaw distal end 1311. In one or more embodiments, an extension of actuation sleeve 260 over a first atraumatic forceps jaw proximal end 1312 and a second atraumatic forceps jaw proximal end 1312 may be configured to cause the first atraumatic forceps jaw distal end 1311 and the second atraumatic forceps jaw distal end 1311 to contact before any other portion of the first atraumatic forceps jaw 1310 contacts any other portion of the second atraumatic forceps jaw 1310.

Figure 14A:
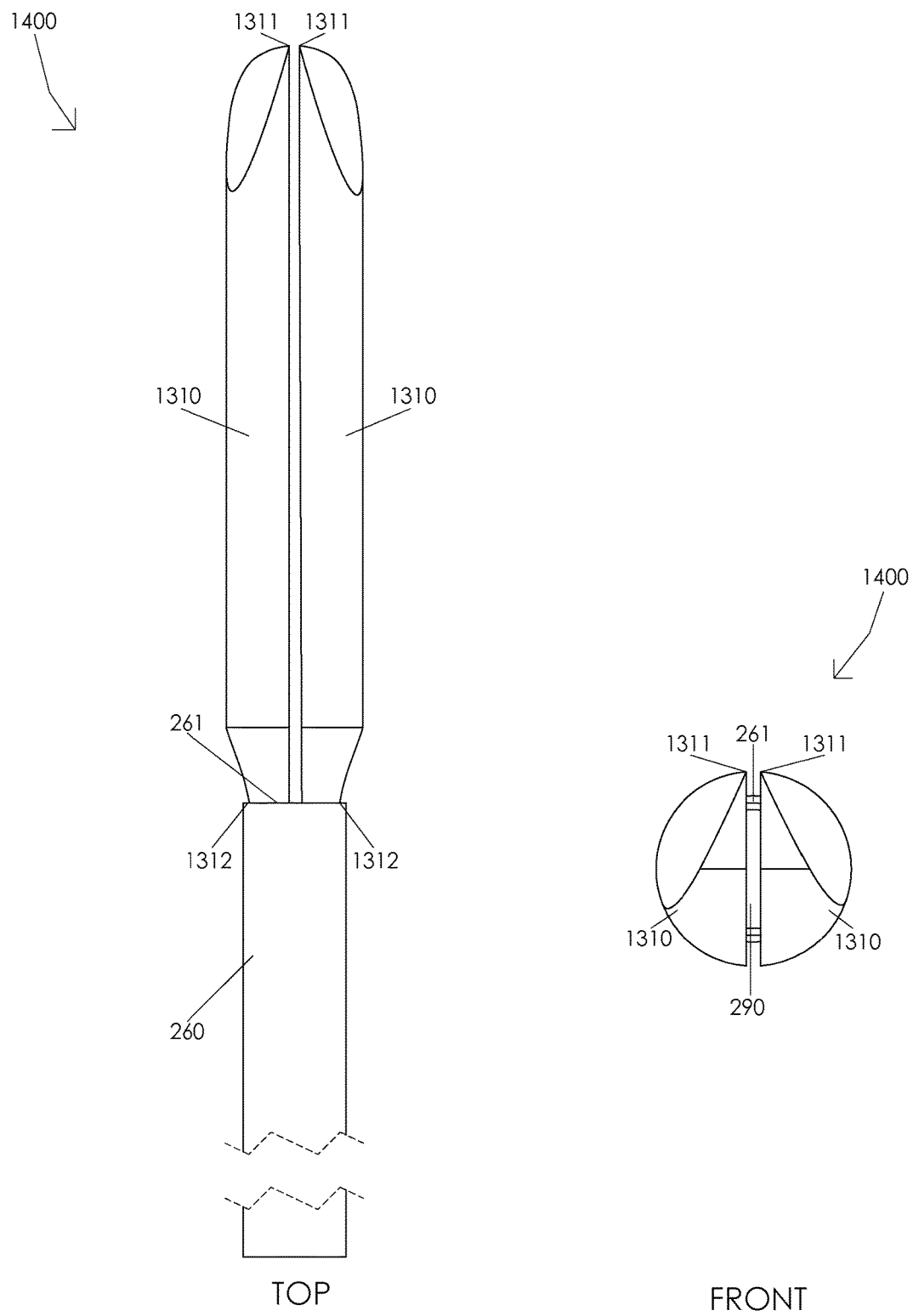
FIGS. 14A, 14B, and 14C are schematic diagrams illustrating a gradual closing of an atraumatic forceps.
Figure 14B:
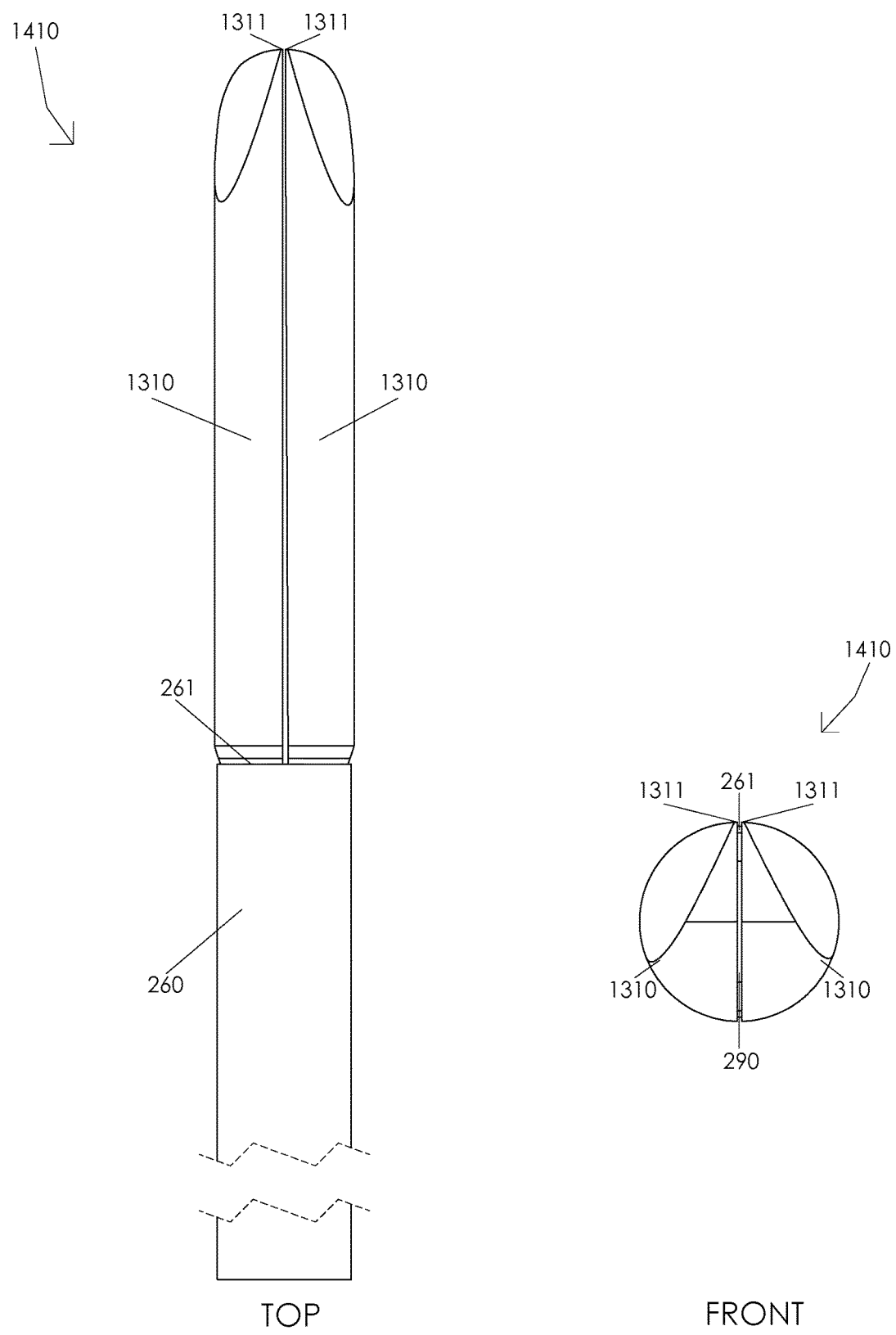
Figure 14C:
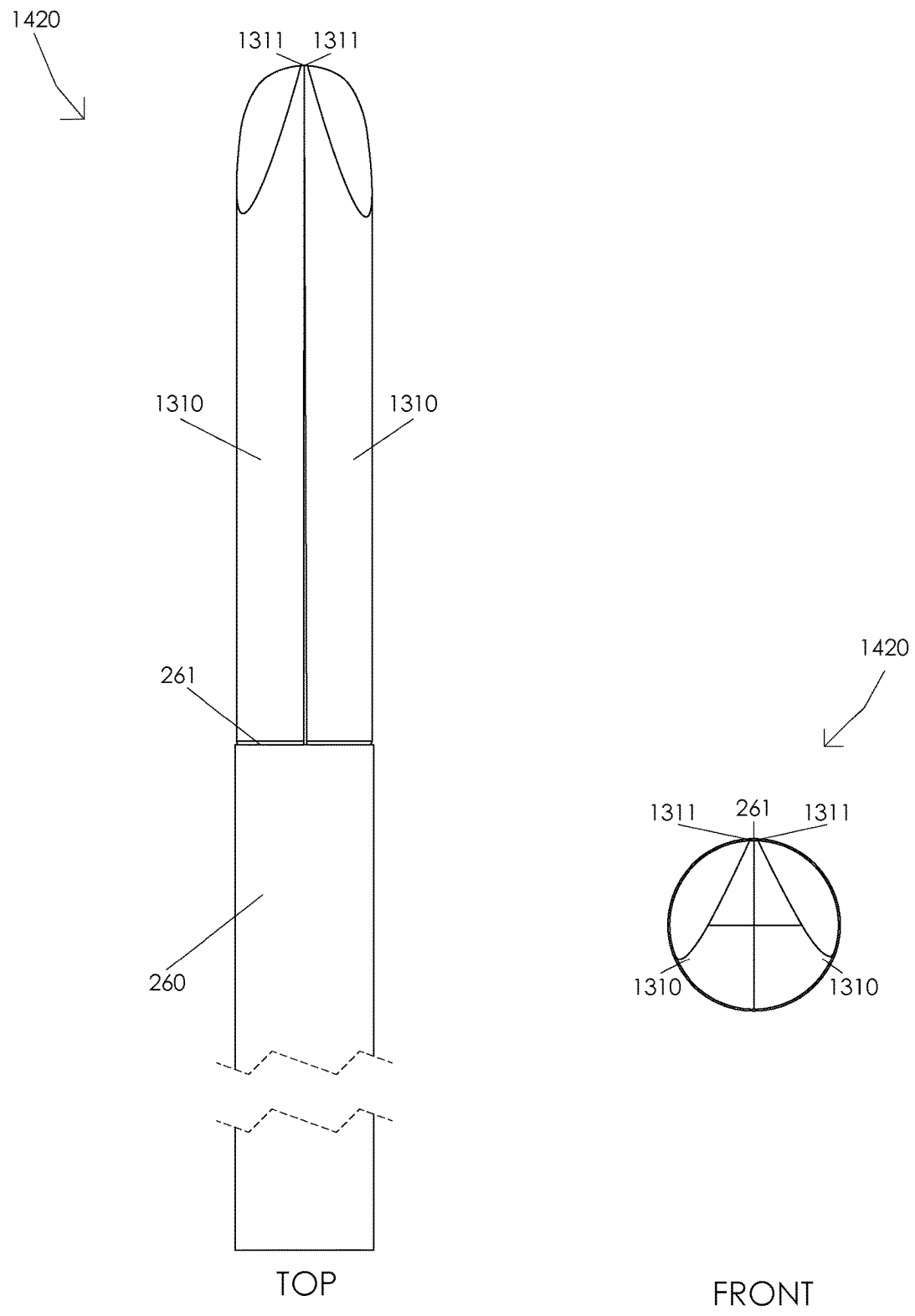

FIGS. 14A, 14B, and 14C are schematic diagrams illustrating a gradual closing of an atraumatic forceps 1300. FIG. 14A illustrates a top view and a front view of an open atraumatic forceps 1400. In one or more embodiments, atraumatic forceps 1300 may comprise an open atraumatic forceps 1400, e.g., when a first atraumatic forceps jaw distal end 1311 is separated from a second atraumatic forceps jaw distal end 1311 by distance 1315. Illustratively, atraumatic forceps 1300 may comprise an open atraumatic forceps 1400, e.g., when actuation sleeve 260 is fully retracted relative to atraumatic forceps jaws proximal ends 1312. Illustratively, atraumatic forceps 1300 may comprise an open atraumatic forceps 1400, e.g., when actuation structure 100 is fully decompressed.

FIG. 14B illustrates a top view and a front view of a partially closed atraumatic forceps 1410. In one or more embodiments, a compression of actuation structure 100 may be configured to gradually close an atraumatic forceps 1300, e.g., from an open atraumatic forceps 1400 to a partially closed atraumatic forceps 1410. Illustratively, a compression of actuation structure 100 may be configured to extend actuation sleeve 260 relative to surgical blank 290, e.g., a compression of actuation structure 100 may be configured to extend actuation sleeve distal end 261 over atraumatic forceps jaws proximal ends 1312. In one or more embodiments, a compression of actuation structure 100 may be configured to decrease a distance between a first atraumatic forceps jaw distal end 1311 and a second atraumatic forceps jaw distal end 1311, e.g., a first atraumatic forceps jaw distal end 1311 and a second atraumatic forceps jaw distal end 1311 may be separated by a distance less than distance 1315 when atraumatic forceps 1300 comprises a partially closed atraumatic forceps 1410.

FIG. 14C illustrates a top view and a front view of a fully closed atraumatic forceps 1420. Illustratively, a compression of actuation structure 100 may be configured to gradually close an atraumatic forceps 1300, e.g., from a partially closed atraumatic forceps 1410 to a fully closed atraumatic forceps 1420. In one or more embodiments, a compression of actuation structure 100 may be configured to extend actuation sleeve 260 relative to surgical blank 290, e.g., a compression of actuation structure 100 may be configured to extend actuation sleeve distal end 261 over atraumatic forceps jaws proximal ends 1312. Illustratively, an extension of actuation sleeve 260 over atraumatic forceps jaws proximal ends 1312 may be configured to close atraumatic forceps jaws 1310 wherein atraumatic forceps jaws 1310 initially contact at atraumatic forceps jaws distal ends 1311. In one or more embodiments, a compression of actuation structure 100 may be configured to gradually close atraumatic forceps jaws 1310 wherein atraumatic forceps jaws 1310 initially contact at atraumatic forceps jaws distal ends 1311. Illustratively, after atraumatic forceps jaws distal ends 1311 initially contact, a compression of actuation structure 100 may be configured to gradually close atraumatic forceps jaws 1310 wherein a contact area between atraumatic forceps jaws 1310 gradually increases. In one or more embodiments, atraumatic forceps jaws 1310 may be configured to close wherein an amount of a first atraumatic forceps jaw 1310 in contact with a second atraumatic forceps jaw 1310 increases gradually from atraumatic forceps jaws distal ends 1311, e.g., atraumatic forceps jaws 1310 may be configured to close wherein an amount of a first atraumatic forceps jaw 1310 in contact with a second atraumatic forceps jaw 1310 increases gradually towards atraumatic forceps jaws proximal ends 1312. Illustratively, a compression of actuation structure 100 may be configured to close atraumatic forceps jaws 1310 starting at atraumatic forceps jaws distal ends 1311 and gradually progressing towards atraumatic forceps jaws proximal ends 1312. In one or more embodiments, a compression of actuation structure 100 may be configured to close a first atraumatic forceps jaw 1310 and a second atraumatic forceps jaw 1310 wherein the first and second atraumatic forceps jaws 1310 initially contact each other at first and second atraumatic forceps jaws distal ends 1311. Illustratively, after the first and second atraumatic forceps jaws 1310 initially contact at first and second atraumatic forceps jaws distal ends 1311, a compression of actuation structure 100 may be configured to cause medial portions of the first and second atraumatic forceps jaws 1310 to gradually contact each other starting at medial portions of the first and second atraumatic forceps jaws 1310 adjacent to first and second atraumatic forceps jaws distal ends 1311.

In one or more embodiments, a surgeon may separate an internal limiting membrane from a retina by grasping the internal limiting membrane with atraumatic forceps jaws 1310, e.g., without damaging the retina. Illustratively, a surgeon may manipulate actuation structure 100 and assembled surgical instrument 200 to approach a retina with atraumatic forceps 1300, e.g., when atraumatic forceps 1300 comprises an open atraumatic forceps 1400. For example, a surgeon may gradually move atraumatic forceps jaws distal ends 1311 closer to a retina until atraumatic forceps jaws distal ends 1311 contact an internal limiting membrane. In one or more embodiments, a compression of actuation structure 100, e.g., by a surgeon, may be configured to extend actuation sleeve 260 over atraumatic forceps jaws proximal ends 1312. Illustratively, a surgeon may grasp an internal limiting membrane with atraumatic forceps jaws distal ends 1311 and no other portion of atraumatic forceps jaws 1310, e.g., to minimize trauma to an underlying retinal tissue. For example, after a surgeon grasps a first portion of an internal limiting membrane with atraumatic forceps jaws distal ends 1311, the surgeon may manipulate the first portion of the internal limiting membrane and compress actuation structure 100 to grasp a second portion of the internal limiting membrane with atraumatic forceps jaws 1310. Illustratively, the surgeon may grasp the second portion of the internal limiting membrane with a portion of atraumatic forceps jaws 1310 located a distance from atraumatic forceps jaws distal ends 1311.

Figure 15A:
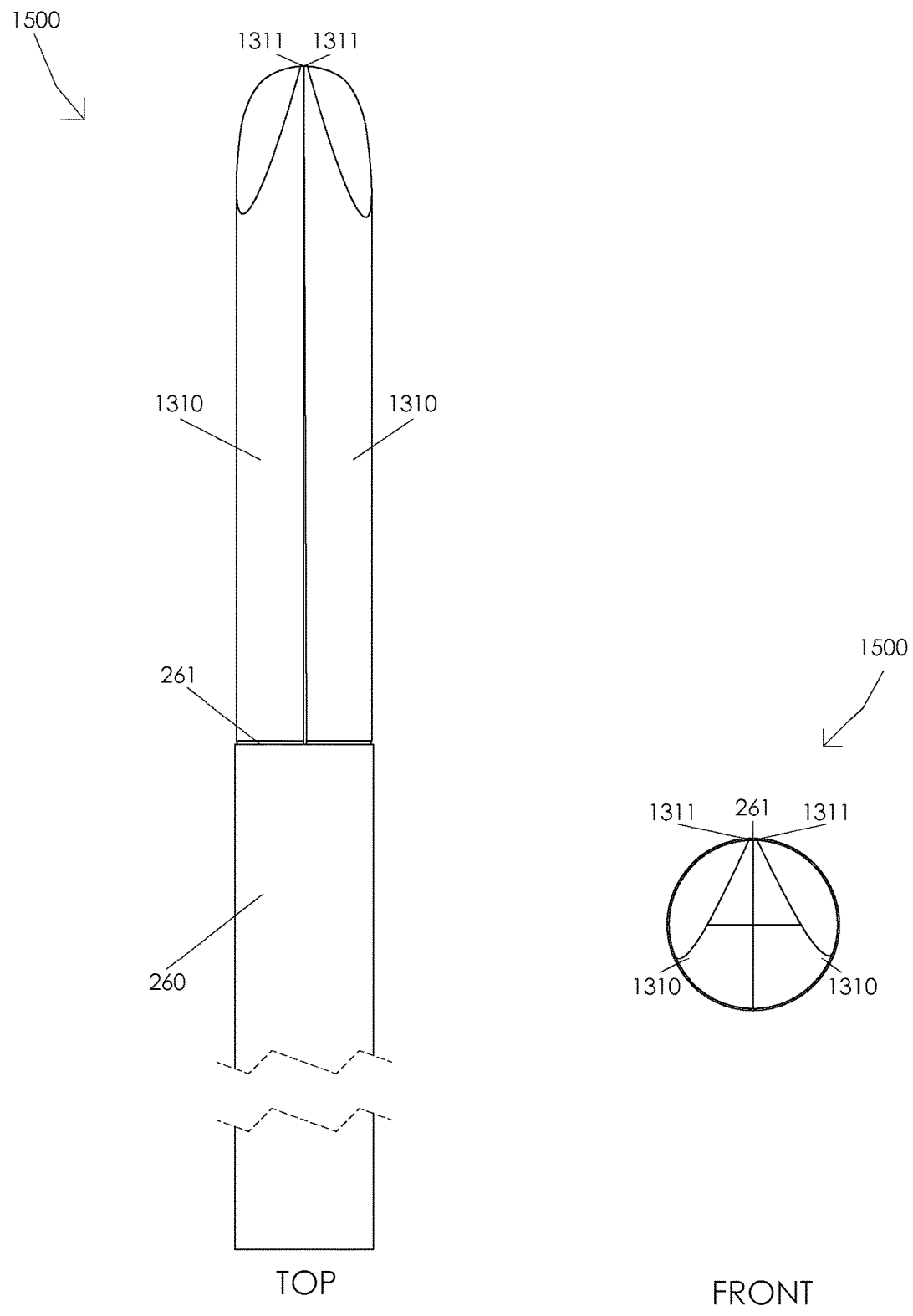
FIGS. 15A, 15B, and 15C are schematic diagrams illustrating a gradual opening of an atraumatic forceps.
Figure 15B:
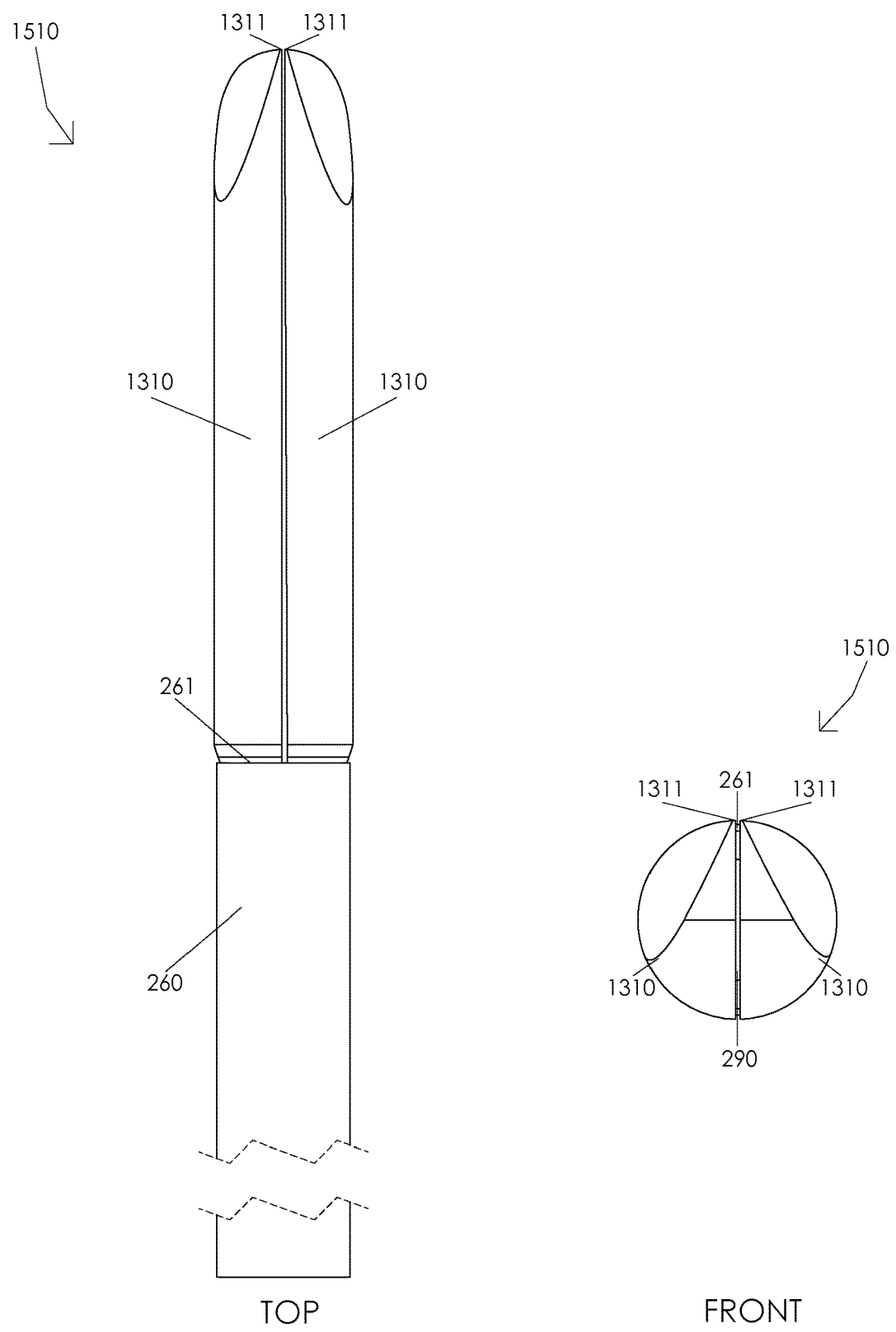
Figure 15C:
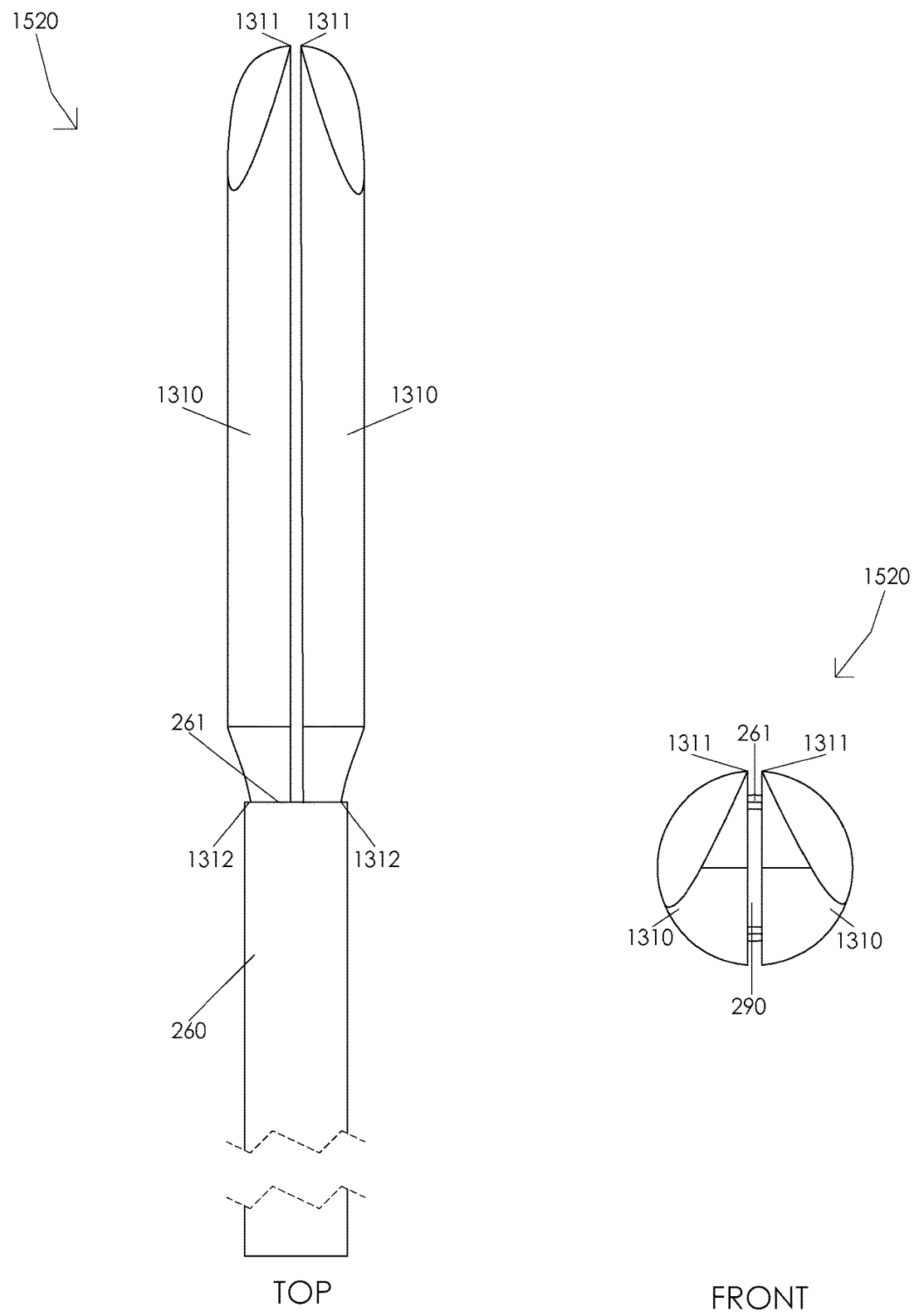

FIGS. 15A, 15B, and 15C are schematic diagrams illustrating a gradual opening of an atraumatic forceps 1300. FIG. 15A illustrates a top view and a front view of a closed atraumatic forceps 1500. In one or more embodiments, atraumatic forceps 1300 may comprise a closed atraumatic forceps 1500, e.g., when a first atraumatic forceps jaw distal end 1311 is adjacent to a second atraumatic forceps jaw distal end 1311. Illustratively, atraumatic forceps 1300 may comprise a closed atraumatic forceps 1500, e.g., when actuation sleeve 260 is fully extended over atraumatic forceps jaws proximal ends 1312. Illustratively, atraumatic forceps 1300 may comprise a closed atraumatic forceps 1500, e.g., when actuation structure 100 is fully compressed.

FIG. 15B illustrates a top view and a front view of a partially open atraumatic forceps 1510. In one or more embodiments, a decompression of actuation structure 100 may be configured to gradually open an atraumatic forceps 1300, e.g., from a closed atraumatic forceps 1500 to a partially open atraumatic forceps 1510. Illustratively, a decompression of actuation structure 100 may be configured to retract actuation sleeve 260 relative to surgical blank 290, e.g., a decompression of actuation structure 100 may be configured to retract actuation sleeve distal end 261 relative to atraumatic forceps jaws proximal ends 1312. In one or more embodiments, a decompression of actuation structure 100 may be configured to gradually separate atraumatic forceps jaws 1310. Illustratively, a decompression of actuation structure 100 may be configured to gradually separate atraumatic forceps jaws 1310 wherein a first atraumatic forceps jaw distal end 1311 contacts a second atraumatic forceps jaw distal end 1311 until all other portions of atraumatic forceps jaws 1310 are separated. In one or more embodiments, a decompression of actuation structure 100 may be configured to separate atraumatic forceps jaws 1310 wherein atraumatic forceps jaws distal ends 1311 are the last portions of atraumatic forceps jaws 1310 to separate.

FIG. 15C illustrates a top view and a front view of a fully open atraumatic forceps 1520. Illustratively, a decompression of actuation structure 100 may be configured to gradually open an atraumatic forceps 1300, e.g., from a partially open atraumatic forceps 1510 to a fully open atraumatic forceps 1520. In one or more embodiments, a decompression of actuation structure 100 may be configured to retract actuation sleeve 260 relative to surgical blank 290, e.g., a decompression of actuation structure 100 may be configured to retract actuation sleeve distal end 261 relative to atraumatic forceps jaws proximal ends 1312. Illustratively, a decompression of actuation structure 100 may be configured to gradually separate atraumatic forceps jaws 1310. In one or more embodiments, a first atraumatic forceps jaw distal end 1311 and a second atraumatic forceps jaw distal end 1311 may be separated by distance 1315, e.g., when atraumatic forceps 1300 comprises a fully open atraumatic forceps 1520.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to any systems where the functionality may be employed. Therefore, it is the object of the appended claims to cover all such variations and modifications as come within the true spirit and scope of the invention.

What is claimed is:

1. A method comprising:
    compressing an actuation structure of an instrument wherein the actuation structure has an actuation structure distal end and an actuation structure proximal end;
    extending a nosecone relative to a surgical blank wherein the nosecone has a nosecone distal end and a nosecone proximal end and wherein the surgical blank has a surgical blank distal end and a surgical blank proximal end and wherein the nosecone has a first barb and wherein the instrument has a tube having a tube distal end and a tube proximal end and wherein the tube distal end interfaces with the first barb and forms a first hermetic seal; and
    extending an actuation sleeve relative to the surgical blank wherein the actuation sleeve has an actuation sleeve distal end and an actuation sleeve proximal end.
2. The method of claim 1 further comprising:
    closing an atraumatic forceps.
3. The method of claim 2 further comprising:
    grasping an internal limiting membrane.
4. The method of claim 3 further comprising:
    separating the internal limiting membrane from a retina.
5. The method of claim 2 further comprising:
    grasping a first tissue.
6. The method of claim 5 wherein the first tissue has a convex surface geometry.
7. The method of claim 5 further comprising:
    separating the first tissue from a second tissue.
8. The method of claim 7 wherein the second tissue has a convex surface geometry.
9. The method of claim 1 further comprising:
    extending the actuation structure distal end relative to the actuation structure proximal end.
10. The method of claim 1 further comprising:
    rotating the actuation structure.
11. The method of claim 1 further comprising:
    sterilizing the instrument in a medical autoclave.
12. The method of claim 1 wherein the actuation structure is manufactured from nylon.
13. The method of claim 1 further comprising:
    decompressing the actuation structure.
14. The method of claim 13 further comprising:
    retracting the nosecone relative to the surgical blank.
15. The method of claim 13 further comprising:
    retracting the actuation sleeve relative to the surgical blank.
16. The method of claim 13 further comprising:
    opening an atraumatic forceps.
17. The method of claim 1 wherein the surgical blank is disposed in a wire lock.
18. The method of claim 1 wherein the instrument has a second barb.
19. The method of claim 1 wherein the tube proximal end interfaces with the second barb.
20. The method of claim 19 wherein the tube proximal end interfaces with the second barb and forms a second hermetic seal.

* * * * *